(12) United States Patent
Botvinick et al.

(10) Patent No.: US 10,750,985 B2
(45) Date of Patent: Aug. 25, 2020

(54) CONTINUOUS ANALYTE SENSOR

(71) Applicant: The Regents of the University of California, Oakland, CA (US)

(72) Inventors: Elliot L. Botvinick, Irvine, CA (US); John Weidling, Long Beach, CA (US); Sean White, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 343 days.

(21) Appl. No.: 15/502,728

(22) PCT Filed: Aug. 6, 2015

(86) PCT No.: PCT/US2015/044063
§ 371 (c)(1),
(2) Date: Feb. 8, 2017

(87) PCT Pub. No.: WO2016/025297
PCT Pub. Date: Feb. 18, 2016

(65) Prior Publication Data
US 2017/0238856 A1    Aug. 24, 2017

Related U.S. Application Data

(60) Provisional application No. 62/052,670, filed on Sep. 19, 2014, provisional application No. 62/035,985, filed on Aug. 11, 2014.

(51) Int. Cl.
*A61B 5/1455*    (2006.01)
*A61B 5/145*    (2006.01)
(Continued)

(52) U.S. Cl.
CPC ........ *A61B 5/14556* (2013.01); *A61B 5/0084* (2013.01); *A61B 5/1459* (2013.01);
(Continued)

(58) Field of Classification Search
CPC . A61B 5/14532; A61B 5/1459; A61B 5/1455; A61B 5/14556; A61B 5/14546;
(Continued)

(56) References Cited

U.S. PATENT DOCUMENTS 5,718,842 A    2/1998 Papkovsky et al.
6,002,954 A    12/1999 Van Antwerp et al.
(Continued)

FOREIGN PATENT DOCUMENTS

JP    2005151972 A    6/2005
JP    2009142657 A    7/2007
(Continued)

OTHER PUBLICATIONS

EP 15832574.6 filed Aug. 3, 2017 European Search Report dated Mar. 6, 2018.
(Continued)

*Primary Examiner* — David J. McCrosky
(74) *Attorney, Agent, or Firm* — Nguyen Tarbet

(57) ABSTRACT

Disclosed herein are embodiments of a continuous analyte sensor that can be used to measure glucose or lactate levels in a patient, along with other analytes. In some embodiments, the sensor can be located in the tissue or a blood vessel of a patient, and a probe can be located on the skin of the patient generally adjacent to the sensor. The probe can detect luminescent signals that originate from the sensor and that are dependent on analyte levels.

43 Claims, 26 Drawing Sheets

(51) Int. Cl.
*A61B 5/1459* (2006.01)
*A61B 5/00* (2006.01)
*A61B 90/98* (2016.01)
*A61B 5/1486* (2006.01)

(52) U.S. Cl.
CPC ........ *A61B 5/1486* (2013.01); *A61B 5/14532* (2013.01); *A61B 5/14546* (2013.01); *A61B 5/4519* (2013.01); *A61B 5/4552* (2013.01); *A61B 5/4845* (2013.01); *A61B 5/4866* (2013.01); *A61B 5/746* (2013.01); *A61B 90/98* (2016.02); *A61B 2562/0238* (2013.01); *A61B 2562/0295* (2013.01); *A61B 2562/046* (2013.01); *A61B 2562/066* (2013.01); *A61B 2562/08* (2013.01)

(58) Field of Classification Search
CPC ........ A61B 5/14735; A61B 2562/0238; A61B 2562/0295
See application file for complete search history.

(56) References Cited

U.S. PATENT DOCUMENTS

| | | | |
|---|---|---|---|
| 6,379,969 | B1 | 4/2002 | Mauze et al. |
| 7,016,714 | B2* | 3/2006 | Colvin, Jr. ........... A61B 5/1459 |
| | | | 600/316 |
| 2003/0186228 | A1 | 10/2003 | McDevitt et al. |
| 2004/0180391 | A1 | 9/2004 | Gratzl et al. |
| 2004/0236250 | A1 | 11/2004 | Hodges et al. |
| 2005/0054028 | A1 | 3/2005 | Teich et al. |
| 2007/0264706 | A1 | 11/2007 | Lee et al. |
| 2007/0281288 | A1 | 12/2007 | Belkin et al. |
| 2008/0219891 | A1 | 9/2008 | McDevitt et al. |
| 2009/0156917 | A1* | 6/2009 | Martini ............... A61B 5/14532 |
| | | | 600/341 |
| 2010/0202966 | A1 | 8/2010 | Gross et al. |
| 2012/0201755 | A1 | 8/2012 | Rozakis et al. |
| 2013/0211212 | A1* | 8/2013 | Stumber ............ A61B 5/14532 |
| | | | 600/316 |
| 2013/0303869 | A1 | 11/2013 | Rebec et al. |
| 2014/0186876 | A1 | 7/2014 | Teich et al. |
| 2014/0275869 | A1* | 9/2014 | Kintz ................... A61B 5/1459 |
| | | | 600/310 |

FOREIGN PATENT DOCUMENTS

| | | |
|---|---|---|
| WO | 2004/060446 A2 | 7/2004 |
| WO | WO2005121785 A2 | 12/2005 |
| WO | WO2012/048150 A1 | 4/2012 |

OTHER PUBLICATIONS

PCT/US2015/044063 filed Aug. 6, 2015 International Search Report and Written Opinion dated Mar. 17, 2016.
Japanese Notice of Rejection for JP Application No. 2017-507817 dated Apr. 8, 2019.

* cited by examiner

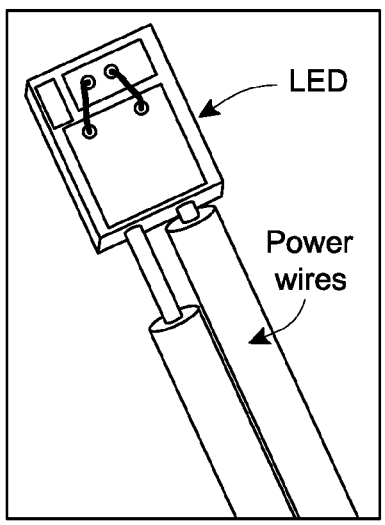 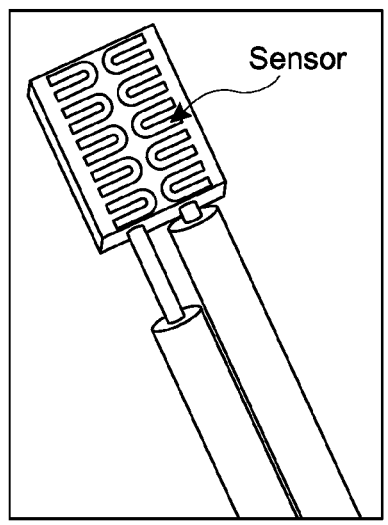
*FIG. 10A*     *FIG. 10B*

CONTINUOUS ANALYTE SENSOR

INCORPORATION BY REFERENCE TO ANY PRIORITY APPLICATIONS

This Application claims from the benefit of U.S. Provisional Application No. 62/035,985, filed Aug. 11, 2015, titled "CONTINUOUS ANALYTE SENSOR," and U.S. Provisional Application No. 62/052,670, filed Sep. 19, 2014, titled "CONTINUOUS ANALYTE SENSOR," the entirety of each of which is incorporated herein by reference.

STATEMENT REGARDING FEDERALLY SPONSORED R&D

This disclosure was made with government support under grant FA9550-10-1-0538 awarded by the Air Force Office of Scientific Research. The government has certain rights in the disclosure.

BACKGROUND

Field

This disclosure relates generally to monitoring analytes in a patient using an implantable device and external probe in order to monitor the health of a patient.

Description of the Related Art

Diabetes

Diabetes mellitus is a metabolic disorder that affects over 350 million people worldwide and the prevalence of diabetes in the world population is increasing at an alarming rate. Maintaining blood glucose levels under tight control represents the most effective way to either prevent the onset of diabetes or reduce the progression of chronic complications in patients suffering from diabetes.

Glycemic control impacts the two most prominent consequences of diabetes: health care costs related to the treatment of diabetes complications and the risk of severe micro- and macro vascular complications associated with the progression of the disease. Importantly, studies have shown that the attainment of tight glucose control can reduce the occurrence of deleterious long-term complications of diabetes. However, with increasingly intensive insulin therapy, the risk of hypoglycemic episodes increases. Self-monitoring of blood glucose (SMBG) is a required component of recommended treatment regimens, required to prevent episodic hypoglycemia and crucial for the effective treatment and reduction of morbidity and mortality in type I diabetes.

However, studies show that patients do not follow recommended treatment guidelines when they require SMBG. This failure to comply is not surprising given that current blood glucose tests, specifically fingersticks, are painful, inconvenient, inaccurate and complicated by the formation of calluses on the fingers. These calluses result in the patient developing poor circulation. Fingerstick devices are widely insufficient for the management of diabetes because they do not provide a continuous measurement of glucose levels, and in fact are periodic at best. In contrast, commercial continuous glucose monitors (CGMs) hold promise to replace finger-stick devices, but currently are only intended to supplement SMBG and are not indicated for making treatment decisions due to their limited accuracy. Current commercial CGMs lack the reliability and accuracy to guide treatment decisions, particularly at low glucose concentrations, or hypoglycemia.

Improved accuracy is required for CGMs to be used in conjunction with an insulin pump, and to fulfill the potential for tight diabetes management. On average 70% of euglycernic (normal glucose) readings from commercial CGMs are within 20% of a reference. Without exception, these CGMs exhibit unreliable and drifting responses over time due to (i) low and varying tissue oxygen concentration, (ii) tissue interferents that affect the electrode, (iii) an inflammatory tissue response resulting in encapsulation of the CGM and (iv) a fibrotic wound response.

Lactate Sensing for Critical Care Management

Lactate, also known as L-(+)-lactic acid or (S)-lactic acid, has been shown to be a powerful biochemical indicator commonly used to stratify risk and to assess adequacy of resuscitation in critically ill patients. Blood lactate has been reported to be a superior resuscitation endpoint compared to other variables such as standard vital signs like heart rate and blood pressure. Changes in lactate levels over time can suggest hemodynamic instability or insufficient response to treatment that may justify additional diagnostic or therapeutic interventions.

In life threatening conditions such as polytrauma, acute myocardial infarction, stroke, and sepsis which all may lead to shock, the speed and appropriateness of therapy administered in the initial hours of onset are likely to influence outcome. These conditions are major healthcare problems, affecting millions of people around the world each year; killing at least one in four people and increasing in incidence. Incorporating lactate measurements in risk stratifying these conditions allows the prompt initiation of life-saving therapy and continuous quantitative measurements so that physicians can appropriately monitor the effectiveness of goal-directed therapy and alter the treatment protocol should response to treatment be insufficient. Current lactate monitoring products are invasive, burdensome to staff and unable to provide critical temporal information of a continuous monitor. Today, measuring lactate is done by either drawing blood from a patient and loading serum samples into a bench top analyzer, or pricking a patient's finger ('finger stick') and using a device with disposable strips similar to those used in blood glucose monitors. Manual lactate measurement is further complicated as a patient is transferred between hospital departments or into a surgical suite. Incorporating frequent manual lactate measurements into this clinical workflow is impractical and would unnecessarily increase staff workload. Further, discrete lactate measurements are simply one point in time, a "picture" rather than continuous measurements analogous to a "video". The single time point measurements lack the temporal data needed to monitor a patient's response to a selected therapy. This is critical to quickly alter therapeutic protocols should a patient not respond to the selected treatment. Real-time monitoring also enables integration of automated alarms to alert medical staff regarding a patient's health status and thus is the ideal method for monitoring a patient's lactate level.

Taking the severe sepsis market alone, there are over 751,000 patients affected resulting in 215,000 deaths annually in the United States. The number of sepsis cases is projected to rise to over one million by 2020. The cost associated with treating these conditions is in excess of $16 billion each year. An aging population that is disproportionately affected by these conditions contributes to an incidence rate that is rising more rapidly than population growth. Early diagnosis and more efficient use of costly healthcare resources are critical to improve outcomes while reducing costs. The continuous monitoring of lactate may be applied to a number of additional areas, including use in surgical recovery, use in trauma patients presenting to the emergency department as well as use by emergency response personnel.

Automated lactate monitoring allows clinicians to detect deteriorating hemodynamic conditions before they manifest clinically and identify instability that is not possible to detect using current clinical parameters (i.e. subclinical or "occult" shock). Additionally, continuous lactate monitoring allows physicians to assess the effectiveness of treatment protocols and facilitate adjustments or alterations to therapeutic approach based on the patient's biological response as assessed by lactate levels and lactate trends. Ultimately, this culminates in improved allocation of resources so that high risk patients are treated as such while reducing staff burden. As an example, Rivers et al demonstrated a 16.5% absolute risk reduction in mortality with early goal-directed therapy including lactate concentration. The ability to monitor therapeutic effectiveness should improve patient outcomes and decrease length of stay, resulting in significantly reduced costs.

Trauma is eminent during acute severe hemorrhagic events common to accidents and combat. In critical events the metabolic state of affected tissues changes from normal oxidative phosphorylation to glycolysis, which creates an imbalance in the production and clearance of lactate, leading to its accumulation. Tissue hypoxia, for instance, causes anaerobic metabolism and is strongly correlated to elevated lactate levels that if untreated, causes shock. Shock is a term describing system wide cell death due to prolonged anaerobic metabolism, which can lead to organ failure and death. Often, patients do not exhibit early symptoms of impending shock, where importantly, early notification would allow early resuscitation and improve patient outcome. Ideal use of continuous lactate monitoring is in military ICUs where an injured soldier exhibiting mild symptoms as compared to a visibly hemorrhagic soldier is triaged under assumption he/she is at lower risk. Often, these "low risk" patients are entering shock that is not detected by current monitoring technologies. It would be ideal to have a trauma alarm that would be sensitive to the soldier's declining health and which sounds-off based on a soldier's increasing lactate levels. This trauma alarm would alert medical professionals to the soldier's health status and accordingly reprioritize him/her as urgent.

Continuous measurement of lactate provides a number of advantages compared to current discrete measurement techniques. The availability of temporal trends in lactate enables tuning of therapies based on a patient's biological response to therapy. This real-time stream of information facilitates incorporation of the data into central patient monitoring systems and enables a high degree of automation based on lactate trends, rates and magnitude.

Blood and tissue lactate levels indicate risk in life-threatening situations such as hemorrhagic shock, sepsis and cyanide poisoning, a major concern of fire departments and the military. Normal blood lactate concentrations range from 0.5-2.2 mM at rest, and levels can increase transiently during/after intense exercise. Sustained blood lactate levels greater than 7-8 mM are associated with fatal outcomes. It has been shown that stabilized or decreasing blood lactate concentrations are predictive of patient survival and blood lactate levels have a role in risk-stratification both in the intensive care unit (ICU) and the emergency department. Rising lactate levels are strongly related to the Sequential Organ Failure Assessment (SOFA) score and consequently early resuscitation in response to increasing blood lactate has been shown to prevent organ failure.

Rising lactate levels are associated with morbidity and mortality in numerous life-threatening conditions including pulmonary embolism, cardiogenic shock, aortic aneurism, carotid artery disease, heart failure, sudden cardiac arrest, acute respiratory distress syndrome, idiopathic pulmonary fibrosis, respiratory failure, and sepsis. It has been Shown that patient morbidity and mortality are related not to a single point measurement of lactate, but to the area under the blood lactate curve of serial measurements as demonstrated in studies of mixed patients and those with sepsis. In these studies, blood was sampled every few minutes and analyzed on-site. This is not typical. Typically, blood draws are taken at most every half hour in extreme cases, if at all, and the blood must then be analyzed by analytic devices often located within the hospital laboratory. Blood measurements require hands-on actions by the treating staff as well as initiative as to when to draw a sample. Such intermittent measurements cannot be used to accurately compute area under the blood lactate curve, and thus are of no use with respect to indicating early resuscitation and saving the lives of severely injured patients.

Currently available products for lactate monitoring consist of approved point of care (POC) 'finger stick' based lactate measurement devices and to a lesser extent, bench top analyzers. POC devices include the Abbott i-Stat, Roche Accutrend Lactate and Lactate Pro. Several companies or groups are developing IV catheter-based continuous lactate monitors. Maquet has the most advanced product called the EIRUS. As previously discussed, there are key disadvantages to this approach. Additionally, these companies, including Maquet, are targeting the surgical market and would be impractical for use in the larger critical care and sepsis markets.

There is no commercial continuous lactate monitor. The state of the art for assessing blood lactate is the YSI Lifesciences 2300 STAT Plus analyzer. Companies such as Abbott and Roche have commercialized 'finger stick' lactate meters. These devices are similar to those used by diabetics to test blood glucose levels. These devices can only measure one time point as directed by the treating staff and thus cannot autonomously alert staff of a patient's failing health.

SUMMARY

Disclosed herein are embodiments of an implanted sensor comprising an enzyme configured to consume oxygen when in the presence of an analyte, a luminescent molecule configured to luminesce, wherein oxygen can bind to the luminescent molecule and at least partially quench the luminescence of the molecule, a plurality of reaction chambers containing enzyme and having the luminescent molecule either within the reaction chamber or in close proximity of the reaction chamber, the plurality of reaction chambers being aligned in a generally repeating pattern, and at least one analyte permeable opening leading to the plurality of reaction chambers wherein the plurality of reaction chambers provides for greater net luminescent intensity from the luminescent molecule.

In some embodiments, the luminescent molecule can be a porphyrin molecule. In some embodiments, the analyte can be glucose and the enzyme is glucose oxidase. In some embodiments, the analyte can be lactate and the enzyme is lactate oxidase.

In some embodiments, the luminescent molecule luminescence can be modulated in accordance with oxygen levels in the sensor. In some embodiments, the sensor can further comprise a reference luminescent molecule configured to luminesce at a different signal than the first luminescent molecule, wherein the reference luminescent molecule is not associated with the enzyme. In some embodiments, the reference luminescent molecule can be located in a reference chamber not fluidly connected to the reaction chambers.

In some embodiments, the sensor can comprise a plurality of enzymes and multiple, distinct luminescent molecules. In some embodiments, the enzyme can be selected from the group consisting of cholesterol oxidase, alcohol oxidase, bilirubin oxidase, ascorbate oxidase, choline oxidase, pyruvate oxidase, sarcosine oxidase, tyramine oxidase, Acyl-CoA oxidase and NADPH oxidase.

In some embodiments, the sensor can further comprise a reflective element. In some embodiments, the sensor can further comprise a radio-frequency identification source. In some embodiments, the sensor further can further comprise a magnetic element. In some embodiments, the sensor can further comprise an electronically conductive element configured to be wirelessly located across tissue. In some embodiments, the sensor further comprise an LED attached to the sensor.

Also disclosed herein are embodiments of a sensor system comprising an implantable sensor configured to be located inside tissue in a patient comprising at least one luminescent molecule configured to associate with oxygen and produce luminescence, and an enzyme configured to react with an analyte, a light source configured to excite the luminescent molecule to luminesce through tissue of the patient, and a probe located adjacent to the sensor comprising a detector configured to receive the luminescence of the implantable sensor.

In some embodiments, the light source and detector can be located on the tissue and the implantable sensor can be located in the tissue. In some embodiments, the light source can be located within the probe, and a light guide can provide light to the sensor. In some embodiments, the implantable sensor can be located between the light source and the probe. In some embodiments, the implantable sensor can be implanted in a patient, the light source is located adjacent to the implantable sensor in the tissue of the patient. In some embodiments, the probe can be located on the tissue of the patient and the light source is located in the tissue of the patient. In some embodiments, the probe and light source can be located in the tissue in the patient. In some embodiments, the probe can be located in the tissue of the patient and the light source is located on the tissue of the patient.

In some embodiments, the probe can comprise an alarm if levels of the analyte fall above a threshold value. In some embodiments, the probe can comprise an alarm prompted by an algorithm operating on current and past sensor values of the luminescence. In some embodiments, the algorithm can operate on an area of the implantable sensor over time.

In some embodiments, light source can be selected from the group consisting of LED, vertical cavity surface emitting laser, or laser diode. In some embodiments, the system can be self-contained with the sensor, light source, and probe.

In some embodiments, the tissue can be skin. In some embodiments, the tissue can be gum (gingiva). In some embodiments, the tissue can be muscle.

In some embodiments, the implantable sensor can comprise a plurality of reaction chambers, each reaction chamber having dye, enzyme, and analyte proximal to one another and wherein each of the reaction chambers is configured to be irradiated approximately simultaneously. In some embodiments the implantable sensor can include multiple enzymes and multiple, distinct luminescent molecules, enabling measurement of multiple analytes from the sensor.

In some embodiments, the implantable sensor and light source can be a first sensor and first light source, and the system can further comprise a second implantable sensor and second light source, the first sensor and light source being paired together and the second sensor and light source being paired together, where the first sensor and light source are configured to analyze a first analyte and the second sensor and light source are configured to analyze a second analyte. In some embodiments, there can be more than two sensor and light source pairs.

Also disclosed herein are embodiments of a sensing method comprising inserting an implantable sensor into a patient, the sensor comprising a luminescent molecule configured to associate with oxygen, and an enzyme configured to react with an analyte, applying a probe onto skin of the patient over the implantable sensor, irradiating the implantable sensor by a light source located adjacent to the implantable sensor inside the patient or adjacent to the probe on the skin of the patient so that the luminescent molecule produces a luminescence, and detecting the luminescence by the probe to determine levels of the analyte.

In some embodiments, the luminescence can exit the patient through the skin. In some embodiments, the sensor can comprise a plurality of reaction chambers, each reaction chamber having dye, enzyme, and analyte, proximal to one another and wherein each of the reaction chambers is irradiated approximately simultaneously. In some embodiments, lifetime of the luminescence can be detected. In some embodiments, a second implantable sensor and a second light source are used.

Disclosed herein are embodiments of a sensor comprising a molecule configured to interact with a target during the molecule's interaction with an analyte, luminescent dye configured to interact with the target and/or product of the interaction and generate a luminescent signal, wherein changes in the signal are related to the concentration of the target, a plurality of reaction chambers comprising the molecule operably coupled to the luminescent dye, which is disposed either within each of the plurality of reaction chambers or outside each of the plurality of reaction chambers, wherein the plurality of reaction chambers are aligned in a generally repeating pattern, at least one target permeable opening/surface in communication with the plurality of reaction chambers, and at least one analyte permeable opening in communication with the plurality of reaction chambers.

In some embodiments, the luminescent dye can be a porphyrin dye. In some embodiments, the analyte can be glucose and the molecule can be glucose oxidase. In some embodiments, the analyte can be lactate and the molecule can be lactate oxidase. In some embodiments, the analyte can be a dissolved gas.

In some embodiments, the sensor can further comprise a reference luminescent dye that luminesces distinctly from the first luminescent dye, wherein the reference luminescent dye is not operably coupled to the molecule. In some embodiments, the reference luminescent dye can be located in a reference chamber not fluidly connected to the plurality of reaction chambers.

In some embodiments, the sensor can comprise at least two different molecules and at least one distinct luminescent dye. In some embodiments, the molecule can be selected from the group consisting of cholesterol oxidase, alcohol oxidase, bilirubin oxidase, ascorbate oxidase, choline oxidase, pyruvate oxidase, sarcosine oxidase, tyramine oxidase, Acyl-CoA oxidase and NADPH oxidase.

In some embodiments, the sensor can further comprise a reflective element configured to be wirelessly located across tissue. In some embodiments, the sensor can further comprise a radio-frequency identification source configured to be wirelessly located across tissue. In some embodiments, the sensor can further comprise a magnetic element configured to be wirelessly located across tissue. In some embodiments, the sensor can further comprise an electronically conductive element configured to be wirelessly located across tissue. In some embodiments, the sensor can further comprise a light source attached to the sensor.

In some embodiments, the target can be oxygen and the interaction can be an oxidative breakdown. In some embodiments, the signal can be an intensity and/or lifetime of the luminescent signal. In some embodiments, the interaction can comprise a breakdown.

Also disclosed herein are embodiments of a sensor system comprising a sensor comprising at least one luminescent dye configured to interact with a target and generate a luminescent signal, wherein signal changes are related to the concentration of the target; a molecule that interacts with the target during an breakdown of an analyte, and a plurality of repeating reaction chambers comprising the molecule, the plurality of repeating reaction chambers in communication with a target permeable opening/surface and an analyte permeable opening, a light source configured to excite the at least one luminescent dye to luminesce, and a probe comprising at least one detector configured to receive the luminescence of the sensor.

In some embodiments, the changes can be changes in the intensity and/or lifetime of the luminescent signal. In some embodiments, the light source can be located within the probe, and a light guide can provide light to the sensor.

In some embodiments, the sensor can be located between the light source and the probe. In some embodiments, when the sensor is implanted in a patient, the light source can be located adjacent to the sensor in the tissue of the patient. In some embodiments, the probe can be located on the tissue of the patient and the light source is located in the tissue of the patient. In some embodiments, the probe and light source can be located in the tissue in the patient. In some embodiments, the probe can be located in the tissue of the patient and the light source is located on the tissue of the patient. In some embodiments, the probe and light source can be located on the tissue of the patient.

In some embodiments, the probe can comprise an alarm if levels of the analyte reach a threshold value. In some embodiments, the probe can comprise an alarm prompted by an algorithm operating on current and/or past sensor values of the luminescence. In some embodiments, the algorithm can operate on a summation or area under the sensor signal over time.

In some embodiments, light source can be selected from the group consisting of light-emitting diode (LED), gas laser, chemical laser, dye laser, metal-vapor laser, solid-state laser, or semiconductor laser.

In some embodiments, the sensor can be implanted in skin. In some embodiments, the sensor can be implanted in a gum. In some embodiments, the sensor can be implanted in muscle.

In some embodiments, each of the plurality of repeating reaction chambers can have luminescent dye, molecule, and analyte proximal to one another, wherein each of the reaction chambers is configured to be irradiated approximately simultaneously. In some embodiments, the sensor and light source can be a first sensor and first light source, the system further comprising a second implantable sensor and second light source, the first sensor and light source being paired together and the second sensor and light source being paired together, where the first sensor and light source are configured to analyze a first analyte and the second sensor and light source are configured to analyze a second analyte.

Also disclosed herein are embodiments of a sensing method comprising inserting a sensor into a patient, the sensor comprising a plurality of generally repeating reaction chambers, each reaction chamber having a luminescent dye configured to interact with a target and generate a luminescent signal wherein changes in signal are related to the concentration of the target, a molecule that interacts with the target during the breakdown of an analyte, and the analyte, proximal to one another, applying a probe onto skin of the patient over the sensor, irradiating the sensor by a light source so that the luminescent dye produces a luminescence, and detecting the luminescence by the probe to determine levels of the analyte.

In some embodiments, the luminescence can exit the patient through the skin. In some embodiments, the changes in signal can be the changes in the intensity anchor lifetime of the signal. In some embodiments, lifetime of the luminescence can be detected. In some embodiments, a second implantable sensor and a second light source can be used. In some embodiments, the light source can be located adjacent to the sensor inside the patient. In some embodiments, the light source can be located adjacent to the probe on skin of the patient.

Also disclosed herein are embodiments of a sensor system comprising a sensor comprising a plurality of light sources, and a plurality of reaction chambers, each of the plurality of reaction chambers located adjacent to one of the plurality of light sources to form a sensor pair, each of the plurality of reaction chambers comprising at least one luminescent dye configured to interact with a target and generate a luminescent signal, wherein signal changes are related to the concentration of the target, and a molecule that interacts with the target during the molecule's interaction with an analyte, and a probe comprising at least one detector configured to receive the luminescence of the sensor, wherein each of the plurality of light sources can be activated independently.

BRIEF DESCRIPTION OF THE DRAWINGS

FIG. 10A illustrates an LED used to backlight an embodiment of a sensor.

FIG. 10B illustrates an embodiment of a sensor glued on-top of an LED.

DETAILED DESCRIPTION

Disclosed herein are embodiments of sensors which can be used to measure different analytes, as well as the chemistry and method of constructions of such sensors. Embodiments of the disclosed sensors can be constructed of flexible, biocompatible materials. Reagents, such as those described in detail below, can be incorporated into the sensors. When the sensors are implanted into a patient or subject, these reagents can undergo chemical reactions with biological analytes in a patient or subject. The reagents in the sensors may also contain reporting agents like luminescent molecules (herein also referred to as dyes) that would indicate if a specific chemical reaction has occurred, typically showing the presence of a particular analyte.

Here luminescence is defined to include, but not be limited to, phosphorescence, fluorescence, bioluminescence and chemiluminescence, though other luminescence can be used as well and the type of luminescence is not limiting. The reporting agent may also bind to biological analytes, such as glucose or lactate as non-limiting examples, to indicate the presence of such biological analytes in a patient or a subject. Further, embodiments of the disclosed sensor may provide details on dissolved gasses or ions, such as oxygen or carbon dioxide, as well as pH or other physiological measurements.

The disclosed sensors can be made of a number of components. For example, a sensor chip can be manufactured which can hold the chemistry for the analysis of the analytes. Further, a probe can also be used to receive information from the sensor chip. Each of the components will be discussed in detail below.

Sensor Chip

In some embodiments, a "sensor chip" can be inserted into a patient. The sensor chip can have a particular channel configuration for holding the chemistry disclosed below in a reaction chamber. Using the below disclosed chemistry and configurations, the sensor chip can be configured to receive radiation from a source and emit radiation that can be based on the level of analyte within the sensor chip, which can be analogous to the amount of analyte within a patient.

Figure 1:
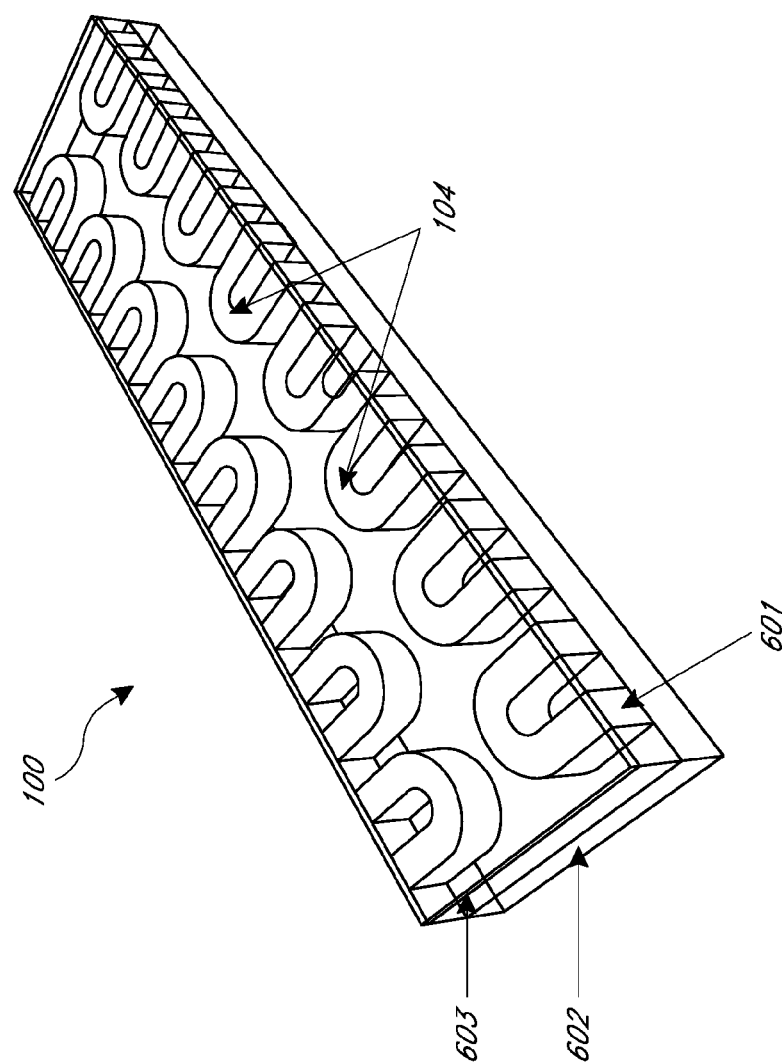
FIG. 1 illustrates an embodiment of a sensor in 3D.
Figure 2:
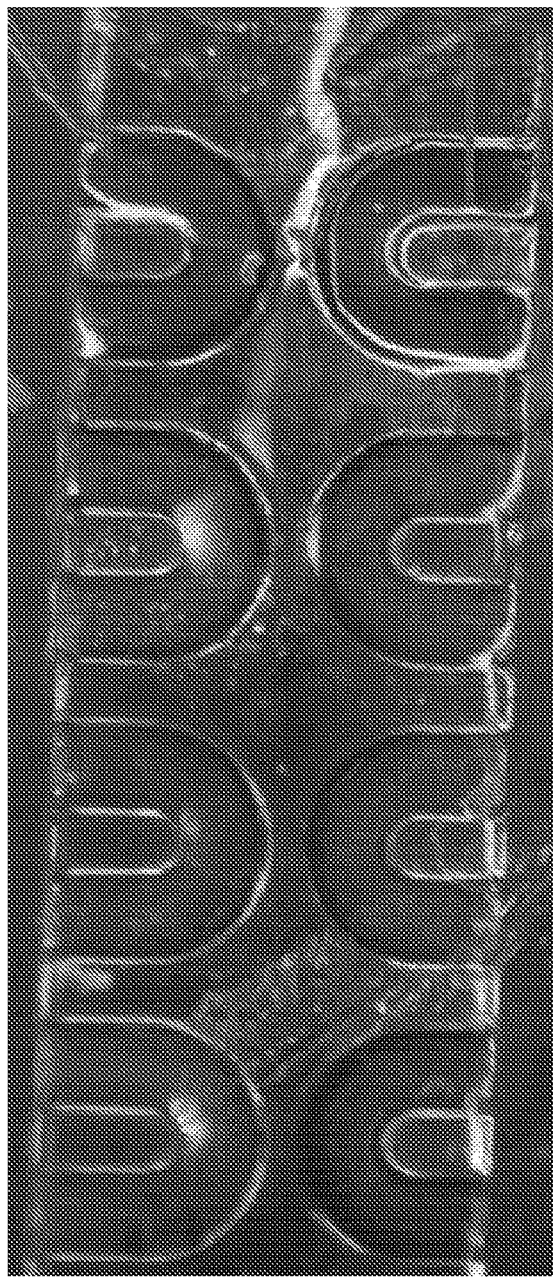
FIG. 2 illustrates a photographic top view of an embodiment of a sensor.
Figure 3:
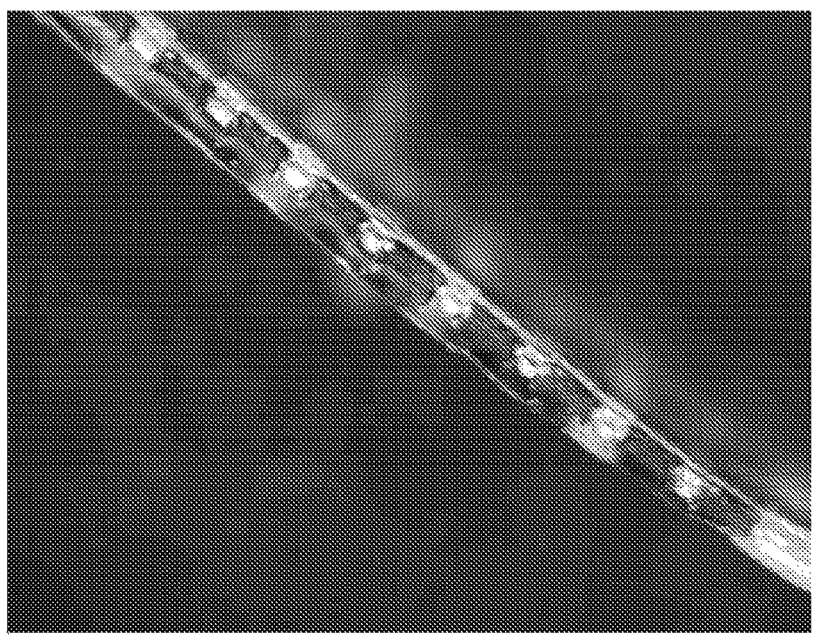
FIG. 3 illustrates a photographic side view an embodiment of a sensor.

An example of the cavity (or reaction chamber) configuration of the sensor chip 100 is shown in FIG. 1. As shown, the cavity 104 can have a generally repeating pattern across a length of the sensor chip 100. Thus, a plurality of cavities 104 can be located proximal, or next to, one another. Further, the sensor chip 100 can have cavities 104 on both longitudinal sides of the sensor chip 100, shown in FIG. 1, thus being generally mirror images across a longitudinal axis of the sensor chip 100. The cavities 104 can be generally size to hold different portions of the sensor chemistry as described below. FIG. 2 is a top view of an embodiment of a sensor chip 100 along. FIG. 3 is a side view of an embodiment of a sensor chip 100. In some embodiments, two adjacent cavities 104 can be used.

In some embodiments, each cavity 104 can have two exit points from the sensor chip 100, though the amount of exits is not limiting. In some embodiments, 5, 8, 10, 16, or 20 different cavities can be used in the sensor chip 100, and the number of cavities 104 is not limiting. This can allow analyte to enter the cavities 104 in two different location. In some embodiments, the analyte 104 does not reach the back of the U, and thus the two legs can form two separate reaction cavities (each having only one entrance/exit). In some embodiments, the cavities 104 can be generally curved, though other shapes can be used as well. In some embodiments, the cavities 104 can extend across the sensor chip 100, and can have exits on both sides of the sensor chip 100. In some embodiments, some or all of the cavities 104 can be connected.

In some embodiments, the entrance to the cavity 104 can have a length/width of approximately 50, 60, 70, 80, 90, 100, 110, 120, or 130 µm. In some embodiments, the entrance to the cavity 104 can have a width/height of less than approximately 50, 60, 70, 80, 90, 100, 110, 120, or 130 µm. In some embodiments, the entrance can be square (e.g. having the same height and width). In some embodiments, the entrance can be rectangular (e.g., having different height and width). In some embodiments, a length of the cavity 104 to the middle (e.g., a leg) can be about 100, 200, 250, 300, 350, 400, or 500 µm. In some embodiments, a length of the cavity 104 to the middle (e.g., a leg) can be less than about 100, 200, 250, 300, 350, or 400 µm.

In some embodiments, the geometry of the cavities 104 can be designed such that it controls the amount and distance of analyte diffusion into the cavity 104. For example: a small surface area entrance region leading to a larger cavity 104 may restrict diffusion, shifting the sensitivity range to higher concentrations. Inversely, a larger surface area entrance region will allow increased diffusion, shifting the sensitivity range to low concentrations.

This configuration can be useful for reducing the size of the reaction chambers, and thus the size of the sensor chip 100. One of the drawbacks of reducing the size of the reaction chambers is that the amount of dye that can be used to obtain signal through tissue is reduced and thus the total intensity of emitted light is reduced as well. In order to overcome this, multiple reaction chambers may be patterned onto one sensor chip 100 to multiply the signal that can be received by the probe, as shown in FIG. 1. The overlapping cavity structure 104 can lead to signal multiplication, and thus to higher signal-to-noise ratios read by a probe and the high signal-to noise provided by the array sensor allows for the use of an inexpensive, large-area amplified photodetector, such as but not limited to a PIN photodiode, rather than a more sensitive detector such as an avalanche photodiode which has a higher cost. In the sensor system where an oxygen sensitive dye is coupled to an oxidase enzyme it may be advantageous to employ an oxygen reference channel to account for the effect of changing oxygen levels on the sensor's output.

Figure 4:
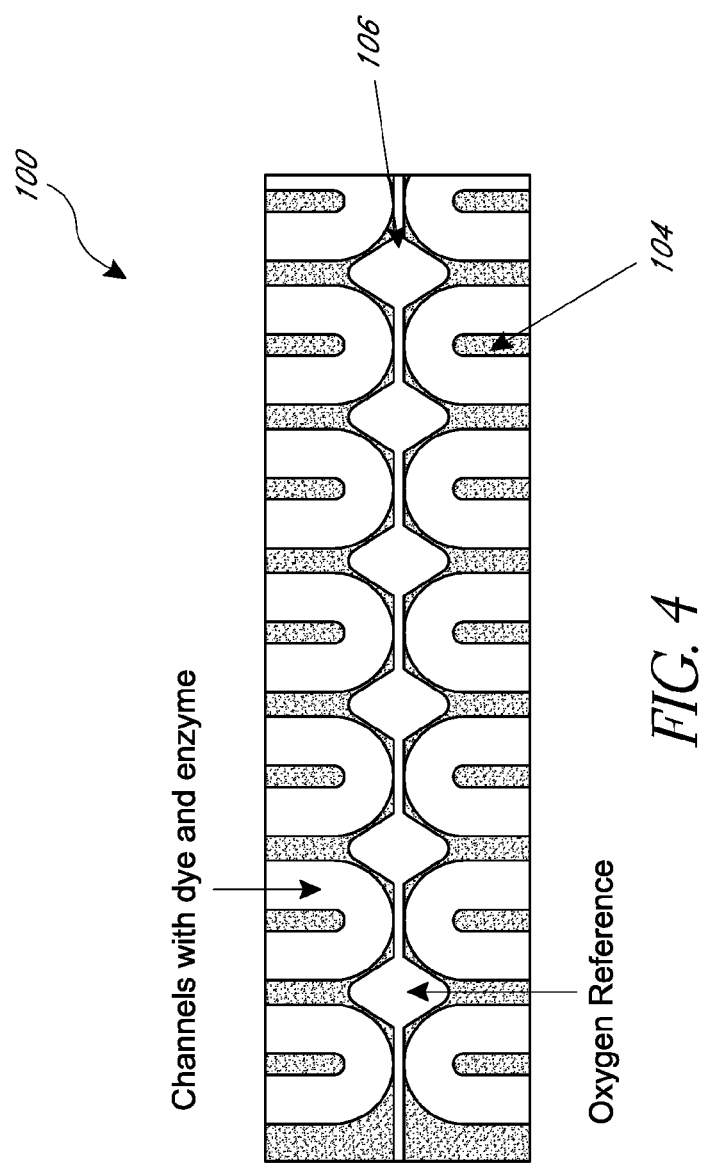
FIG. 4 illustrates an embodiment of a sensor with a built-in internal oxygen reference.

In some embodiments, an oxygen reference may be included on-chip and may be used to compensate for changes in tissue oxygenation around the sensor not due to changes in analyte-of-interest concentration. An example design is shown in FIG. 4. As shown, the oxygen conduit 106 can pass down the middle of the sensor chip 100 and can contain larger diameter areas for storing the oxygen reference. However, this is only an example configuration, and the oxygen conduit 106 can be located in different portions of the sensor chip 100.

An oxygen conduit similar to the oxygen conduit described in U.S. Pat. No. 7,146,203, hereby incorporated by reference in its entirety, may be implemented on the sensor described in this application.

The sensor chip 100 can have a height of about 100, 110, 120, 130, 140, 150, 160, or 170 µm. The sensor chip 100 can have a height of less than about 100, 110, 120, 130, 140, 150, 160, or 170 µm. In some embodiments the sensor chip 100 can have a width/length of about 140, 160, 170, 180, 190, 200, 210, 220, 230, 240, or 250 µm. In some embodiments the sensor chip 100 can have a width/length of less than about 140, 160, 170, 180, 190, 200, 210, 220, 230, 240, or 250 µm.

Probes

On-Tissue Probe

In some embodiments, a probe with a light source may be used to excite a reporting agent, like the porphyrin dye discussed below, in an implanted device and the same probe may contain a photodetector that detects remitted light from the reporting agent that can be contained in the device. Different sources of light with differing wavelengths may be installed on the probe. As discussed below, the dyes can be phosphorescent, fluorescent, or any other type of luminescent dye and the light emitted by the dye is not limiting.

In some embodiments, a probe that may detect a reporting agent in the sensor can be placed on the surface of the tissue and aligned with the sensor beneath in order to take measurements from the sensor. The probe may contain a light source that emits light, such as visible, UV, or infrared or other radiation, that passes through the tissue thereby exciting one of the reporting agents in the sensor. Measurements may be taken by measuring the light that is emitted back through the tissue by the excited reporting agent. The probe could contain a detector that may measure the light emitted back through the tissue by the excited reporting agent.

Analyte measurement using embodiments of the above sensors or sensor chips can be accomplished by optical excitation of a reagent within the sensor. Remitted light from the sensor can then be transmitted through the surrounding tissue and can then be detected using a photodetector within the probe. Probe embodiments include, but are not limited to, the following description. A probe can utilize light emitting diodes (LEDs) to optically excite an oxygen-sensitive porphyrin dye within the sensor. LED emission wavelength (color) may be chosen to minimize optical scattering and absorption within tissue while maintaining a maximum overlap with the dye's absorption spectrum. In the case of Platinum Tetrabenzo Porphyrin, red light emitting LEDs can be an appropriate choice. The porphyrin dye's luminescent lifetime and/or intensity can then be dependent upon the concentration of oxygen within the sensor or sensor chip's local environment. The LED's can have a length/width of about 150, 160, 170, 180, 190, 200, or 210 µm and a height of about 50, 60, 70, 80, 90, or 100 µm. The LED's can have a length/width of less than about 150, 160, 170, 180, 190, 200, or 210 µm and a height of about 50, 60, 70, 80, 90, or 100 µm, but the dimensions are not limiting.

Measurement of the porphyrin dye's luminescent lifetime and/or intensity has been achieved by measuring light emitted by the dye as a function of time shortly after pulsed excitation using a photodiode placed on or near the skin above the implanted sensor and using an appropriate mathematical fit for the acquired data (e.g. decaying exponential). It can be advantageous that. (1) excitation of the porphyrin dye be ceased and (2) measurement of its lifetime or intensity begin on a time scale significantly less than the luminescence lifetime of the dye so that the dynamics of the dye can be measured before dye luminescence has ended. Additionally, the signal to noise ratio of probe measurements can be greatly enhanced by selective rejection of excitation and ambient light, as can be accomplished using a filter with minimal transmission at the excitation light wavelength(s) and high transmission at the emission wavelength(s) of the dye(s).

Excitation of the dye within the sensor can be achieved by using a variety of light sources, including but not limited to, light-emitting diodes (LEDs) and laser diodes. Specifically, an LED is illuminated by applying power in square wave profile. This effectively causes the LED to 'blink' on and off. Following the falling edge of the square wave, the LED can be off and no longer exciting the dye, however, the dye can be undergoing luminescent decay because it has been optically excited. A photodetector with accompanying hardware to record collected information can be used to detect this optical dye luminescence signal. Luminescent intensity decay can be characteristically exponential in nature (decaying exponential), and the acquired luminescence signal can therefore fitted an appropriate mathematical function (i.e. $e^{t/\tau}+B$) to compute a characteristic decay lifetime ($\tau$).

Mathematical fitting can be achieved using a variety of methods, including but not limited to least-squares, least absolute residual, bisquare, and phasor methods. It can be advantageous to use a light source for excitation that has a falloff time much shorter than the expected luminescence decay lifetimes of the dye(s) used. If this is not the case, the calculated dye lifetime may be erroneously increased. It can also be advantageous to not begin collecting or processing luminescence data until the excitation source has reached an appropriately minimal intensity. Additionally, excitation of the dye followed by collection of the luminescence signal from the dye can be repeated such that the recorded decays can be averaged together to increase the reliability of the resulting mathematical fit.

Figure 5:
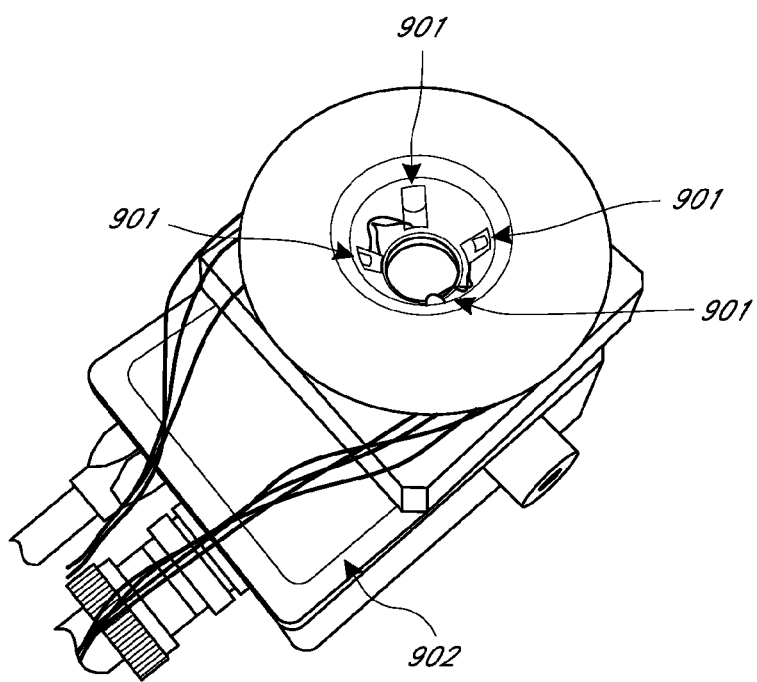
FIG. 5 illustrates an embodiment of a handheld probe that incorporates a light source used to excite the sensor and a detector on the device used to detect the luminescent emission from the sensor.
Figure 6:
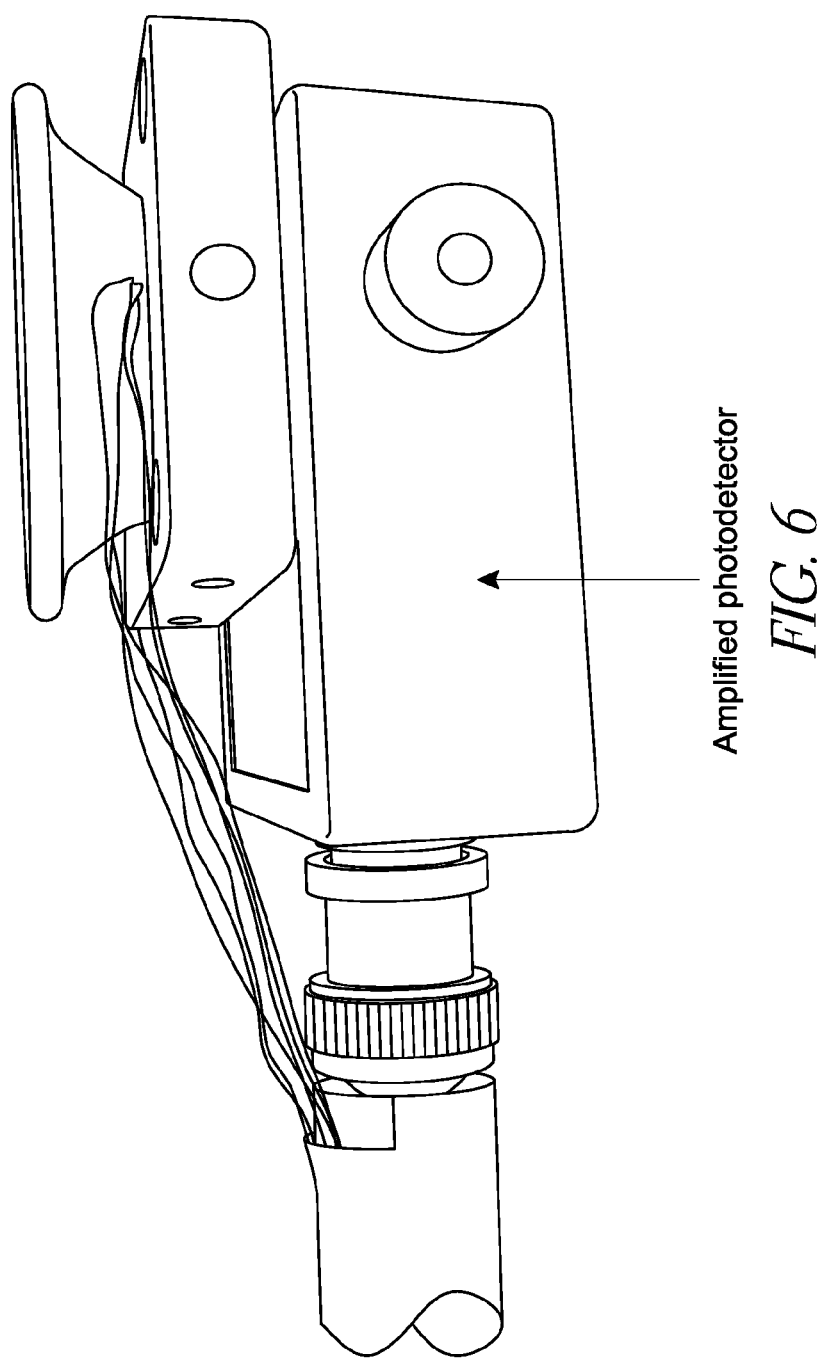
FIG. 6 illustrates the side view of an embodiment of a handheld probe in FIG. 5.

As shown in FIG. 5, embodiments of the probe can include the use of an 'optical stethoscope', where LED's can be mounted at an angle to aim the center of their light beams directly at a sensor implanted beneath tissue while a detector sits in between the LED's to collect the sensor's emitted light. As shown, there are a total of four LEDs diodes 901 that may be the same or of differing wavelengths, though the number of diodes is not limiting. Further, one or more amplified photodiodes with a long-pass or band-pass optical filter 902 can be used as well, FIG. 6 is a side view of the probe as seen in FIG. 5. In some embodiments, the sensor chip may not be tether to the probe, and may be fully implanted into the patient.

Figure 7:
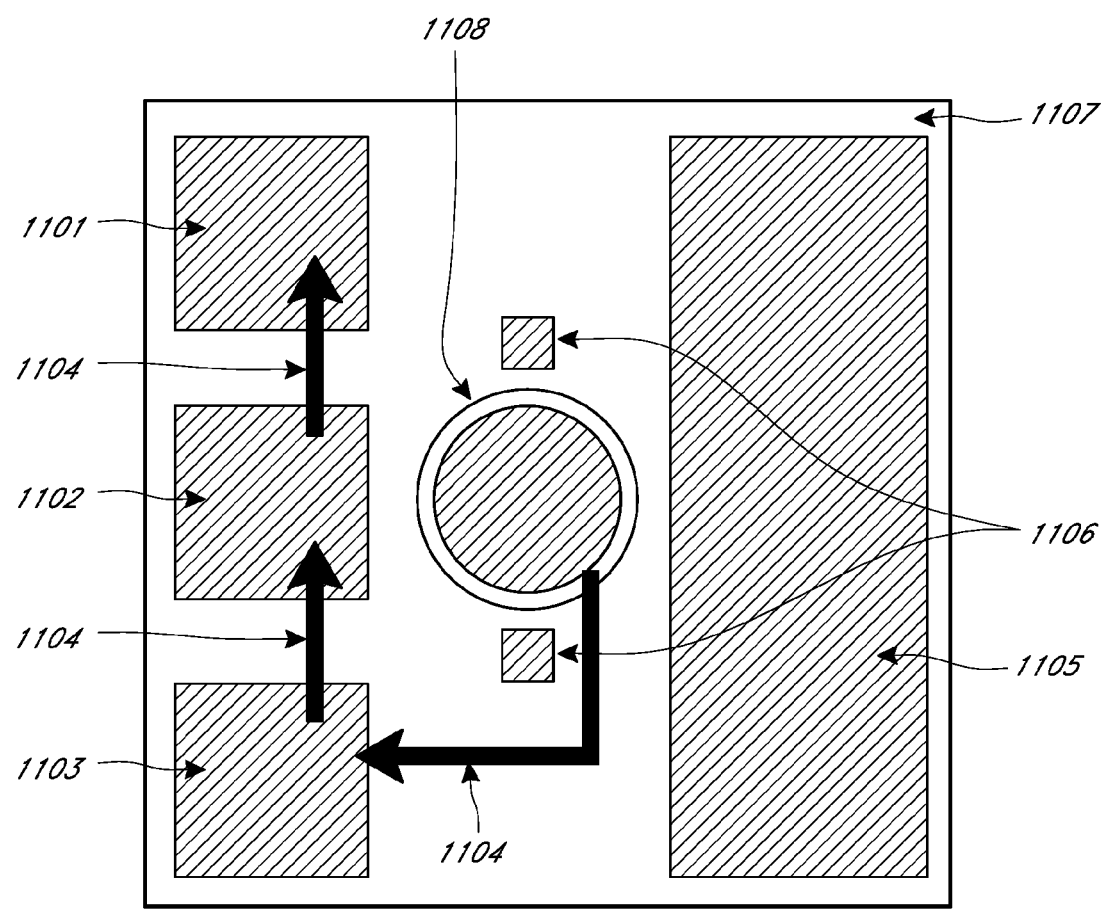
FIG. 7 illustrates the schematic for an embodiment of a self-adhesive probe to measure activity of reporting sensor.
Figure 8:
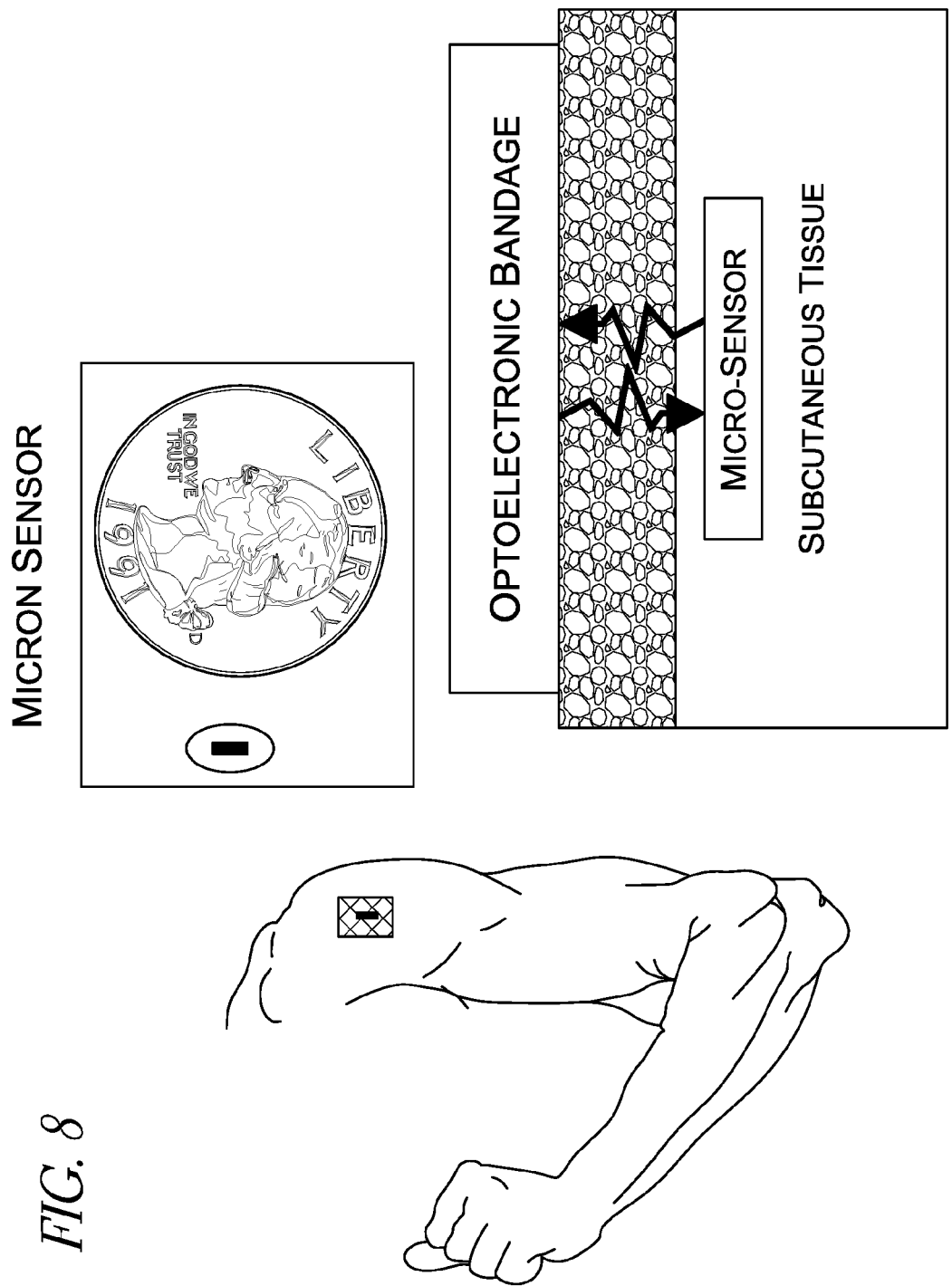
FIG. 8 illustrates the size of an embodiment of a sensor relative to a quarter and how the sensor may be read with a measurement probe in the form of an optoelectronic bandage.

FIG. 7 shows the schematic for the probe that may be translated into a self-adhesive or "band-aid probe". 1101 is a wireless data emitter. 1102 is hardware for analog to digital conversion and raw data processing. 1102 may include, but is not limited to, application-specific integrated circuits or field-programmable gate array. 1103 is a circuit for signal amplification and conversion (if necessary) and may include, but is not limited to, a transimpedance amplifier. 1104 shows the schematic for the transmission of the signal from the photodetector to its processing through to 1103, 1102 and 1101, 1105 is the battery or power source. 1106 are the light sources for dye excitation (or power source connection for light sources located off the band-aid probe circuit board). 1106 may include, but not limited to, a single or plurality of LEDs= or other sources to excite a dye. 1107 is the substrate providing mechanical connection between detector components which may or may not contain electrical connections between said components. Said substrate may be rigid or flexible. 1108 is a photodetector for detection of dye emission. The photodetector may include a spectral filter with a transmission spectrum appropriate for isolating signal from one or more dyes. FIG. 8 illustrates the size of the sensor relative to a quarter and how the sensor may be read with an optoelectronic band-aid probe.

Backlight Probe

Figure 9:
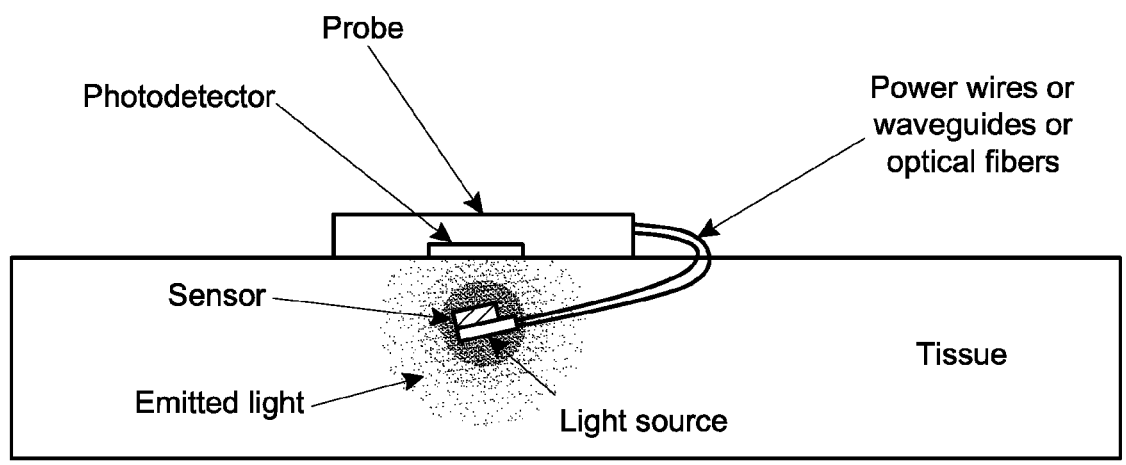
FIG. 9 illustrates an embodiment of an implanted sensor backlit with a light source and the sensor/light source combination tethered to the probe, which serves as a power source or a light source.

FIG. 9 illustrates an embodiment of a sensor and probe. A light source, or multiple light sources, may be incorporated onto embodiments of the sensor. In FIG. 9, the light source, such as an LED, can backlight the sensor so that it may act as an excitation source for the luminescent dyes in the sensor. A wire or a multitude of wires may be connected to the light source to power the light source. Power or light may be supplied, for example, by an external source or by the measurement probe, which may have its own power or light source. In this configuration, the probe can be placed above the sensor for transdermal detection of luminescent signal following optical excitation of sensor. FIG. 10A shows the LED light source connected to white and black power wires and FIG. 10B shows the sensor glued onto the face of the LED using silicone adhesive. In some embodiments, the wires can have a height of about 200, 220, 240, 260, 280, 300, 320, or 340 μm. In some embodiments, the wires can have a height of less than about 200, 220, 240, 260, 280, 300, 320, or 340 μm.

The implanted light source can be powered, for example, by utilizing power wires that can traverse the skin's surface and connect to an appropriate power source, or be unpowered, by utilizing a light source that can be powered wirelessly via induction or by using an optical fiber or waveguide that traverse the skin's surface and connects to the sensor through which excitation light can be transmitted.

Utilizing the excitation strategy described above offers several advantages. First, the excitation light meant to excite the luminescent dye within the sensor is no longer required to propagate through the same thickness of tissue before reaching the sensor as would be required using transdermal excitation. As a result, the efficiency of excitation is increased, and more sensor luminescence can be detected back through the skin to the probe, i.e., a greater signal to noise ratio can be achieved. As a result, more compact light sources capable of generating smaller light fluence and which use less power can be used. Additionally, because greater excitation efficiency increases detectable luminescent signal from the sensor, a wider variety of luminescent dyes, specifically those with lower quantum efficiencies such Pd-core metalloporphyrins as compared to Pt-core metalloporphyrins, may be used. Second, if wires, waveguides, or optical fibers are used, they can also be utilized as a simple tether far retrieval of the light source/sensor combination during acute study.

A variety of light sources can be used in the combined light source/sensor embodiment described above. One potentially advantageous light source is an LED. This is due in part to the fact that LEDs can be manufactured commercially into very small form factors, offer a large variety of output wavelengths, and require relatively little power to achieve appropriate light output for optical excitation of the sensor. During implantation, utilizing as small of an LED as possible is desirable to minimize patient discomfort and implantation site trauma. In the embodiment shown in FIG. 10A a commercially available LED with dimensions 1.70 mm×1.30 mm×0.96 mm (L×W×H) is used. Successful combined light source/sensor embodiments have utilized commercially available LEDs as small as 1 mm×0.6 mm×0.2 mm (L×W×H). These LED sizes are meant to elucidate the flexibility of LED size choice, and do not represent constraints regarding their usage.

In some embodiments, biocompatibility of the light source/sensor combination can be manipulated by first coaling the light source and any accompanying wires in a biocompatible material before placing the sensor on or near the light source. The material used to coat the light source can have a relatively low absorption coefficient at the wavelengths used by the light source to optically excite the sensor. Potential biocompatible materials include silicone polymers such as PDMS. Such polymers can also be used to affix the sensor to the light source. However, in some embodiments such a coating may not be used.

Figure 11:
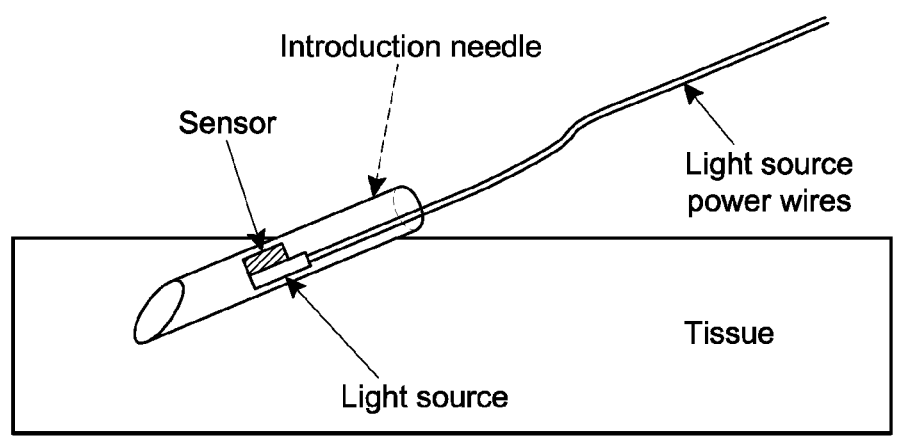
FIG. 11 illustrates how an embodiment of a sensor and light source combination may be implanted with an injection needle.

Embodiments of the combined sensor and light source can be introduced into the tissue of interest, for example, through surgical implantation or by using a needle tip for introduction as seen in FIG. 11, though the particular implantation mechanism is not limiting. In this example, the sensor and light source are affixed to one another and placed into the lumen of a needle. The sensors can be small enough to fit into a sixteen gauge needle or smaller. The target implantation depth in tissue is around 1-5 mm, allowing the sensor to interact with the interstitial fluid of the tissue, although this implantation depth is not limiting. However, embodiments of the sensor could be located intravascularly as well. The needle is then used to introduce the sensor and light source into the tissue (FIG. 11), after Which the needle is removed from the tissue, leaving behind the sensor and light source (FIG. 9). Thus, as shown, a needle may be used to inject the sensor and light source under the patient's skin for data collection using appropriate light detection and a data processing hardware. If wires are used to power the light source, or if a waveguide or optical fiber is used to transmit light to the sensor, they can be left to traverse the tissue above the sensor.

In some embodiments, sensors can be implanted so that no part of the sensor or probe crosses the outer layer of the skin, and thus is fully contained within the patient. In some embodiments, the sensors may also have an attachment that crosses the skin. This attachment may allow the implanted sensor to be easily removed by gripping on the attachment that is above the skin and pulling the attachment and sensor so that it is removed easily from the patient.

In some embodiments, the sensor can be applied as a self-contained patch. The sensor itself can be located within the skin of a patient, such as in interstitial fluid or blood. The sensor can then be connected to a probe, which can include a photodetector. The probe can provide either light to the sensor, or power to a light source implanted with the sensor, thereby illuminating the sensor to provide luminesce to the detector. As discussed below, the entire patch can be very small, such as that of a band aid. In some embodiments, the sensor can be significantly smaller than a quarter, such as shown in FIG. 8. In some embodiment, luminescence from the sensor can pass through the skin of a patient and out to the detector.

Multiple LED Probe

By utilizing an excitation source that is located beneath the skin and proximal to the sensor(s) of interest, an alternative methodology for acquiring data from a reference, sensor(s) sensitive to additional analytes, or both can be performed. Specifically, a single light source and sensor pair can be utilized to measure an analyte of interest as described previously. Further, a second light source and sensor pair can then be placed below the skin's surface as close or as far from the first light source and sensor pair as desired. This configuration is shown in FIG. 12.

The second sensor may be used as a reference only, or may be used to measure an additional analyte of interest, such as those discussed in detail above.

In some embodiments, a plurality of tight source and sensor pairs can be used, where each sensor may, but need not, measure a different analyte. For example, 2, 3, 4, 5, 6, 7, 8, 9, or 10 sensor pairs can be used. In some embodiments, greater than 2, 3, 4, 5, 6, 7, 8, 9, or 10 sensor pairs can be used. In this manner, each sensor pair may provide for measurement of a different analyte or gas or some sensor pairs may measure the same analyte.

Figure 12:
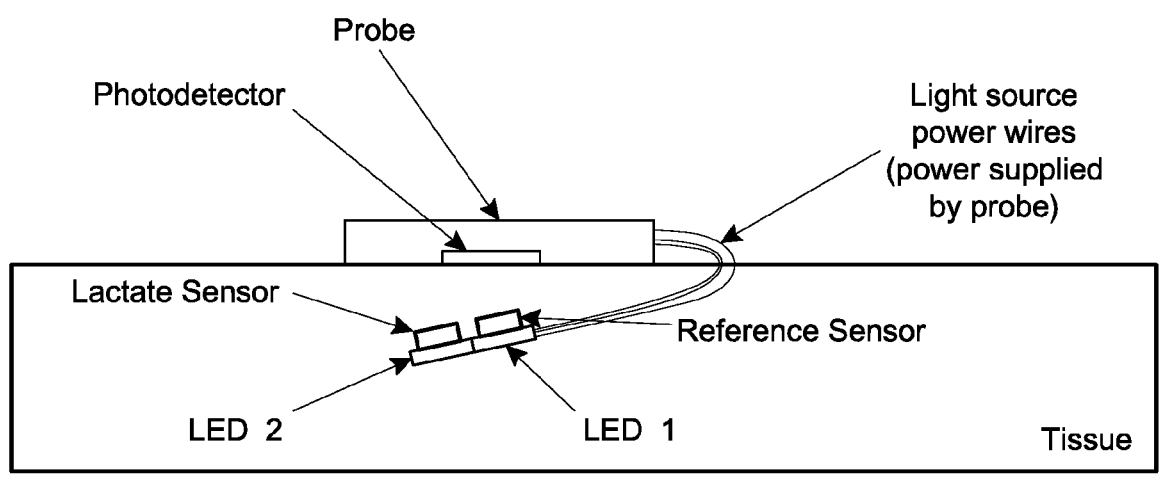
FIG. 12 illustrates an embodiment of a multi-LED sensor.

An embodiment of this concept using two LED light source and sensor pairs is shown in FIG. 12, where one sensor is sensitive to lactate and one sensor is used as an oxygen reference. In some embodiments, each sensor can analyze a separate analyte at the same time. Thus, the LEDs could be activated one at a time to select which analyte will be measured, or both can be activated to measure two analytes. As shown, both LEDs and sensors are inserted into the tissue, though as discussed above other approaches can be used. A photodetector can be located on top of the tissue to receive signal from the sensors. Light output from LED1 and LED2 can be controlled independently or simultaneously, enabling significant optical excitation of only one sensor at a time. In this manner, luminescence from the reference sensor can be temporally and spatially decoupled from luminescence from the lactate sensor.

Advantages of the aforementioned methodology include, but are not limited to, the fact that design of each sensor can be simplified by merit of the fact that each sensor need only measure a single analyte. Additionally, because each sensor can be optically excited independently in time, the same oxygen-sensitive dye can be used in each sensor as each sensor can be temporally decoupled. This can additionally simplify spectral filtering of the detected light as multiple emission spectrums no longer need to be separated from one another. An additional advantage is the fact that light source and sensor pairs can be placed as close or as far from one another as desired. Further, these pairs can be moved after implantation in tissue. This can enable multiple analyte and reference measurements to be performed in either the same or in different tissue microenvironments.

In some embodiments, the sensor in each light source and sensor pair can be placed in direct contact with the emission surface of each respective light source, thereby minimizing cross-talk (e.g., light from one source optically exciting luminescence from a nearby sensor not paired with the source). Additionally, light source and sensor pairs can be placed in the tissue adequately far from one another as to reduce the amount of excitation light from one light source and sensor pair reaching another, reducing the chance of cross-talk between the two sensors. Further, sensors that contain dye with a very high absorption coefficient may be used such that a satisfactory amount of light emitted by each light source is absorbed by the intended sensor. Additionally, the emission angle and direction of light emission from each light source may be adjusted to minimize excitation light from one light source and sensor pair reaching an unintended sensor. In a variation, the light source and sensor pair may be optically coupled (and isolated from additional pairs) though one or more optical fibers.

In some embodiments, multiple sensors can be used that all use different enzymes, but use the same luminescent molecules. Thus, each sensor can be measured uniquely by illuminating only its paired LED.

Chemistry

Enzymes

Embodiments of a glucose sensor may consist of a layer of porphyrin dye in the shape of a rectangle with a hydrogel containing glucose oxidase, in the same shape, in contact with the dye layer. As discussed above, the sensor is not limited to a rectangular shape, and other shapes can be used as well. The glucose oxidase reacts with glucose and oxygen, producing gluconic acid and hydrogen peroxide. An enzyme can be incorporated that can be operably coupled to a luminescent molecule. For example, the enzyme can be within a diffusion distance to the luminescent molecule in order to interact with oxygen utilized in the reaction chamber.

| Enzyme | Reaction |
|---|---|
| Glucose Oxidase (GOX): | glucose + $O_2$ → gluconic acid(GA) + $H_2O_2$ |

The probe can measure the consumption of oxygen due to the presence of glucose, thus using oxygen concentration measurement as an indirect measure of glucose concentration via a calibration. For example, if the reaction chamber containing the dye and enzyme hydrogel is enclosed except for two openings that are permeable to fluid containing glucose (FIG. 1, 601), then the glucose can diffuse into the reaction chamber along the length of the chamber and set up a gradient in concentration along its length due to diffusion from the outside and consumption on the inside of the chamber (consumed by the glucose oxidase). As the glucose is consumed, oxygen is also consumed, and so by measuring the oxygen level of the reaction chamber by reading the emission of the porphyrin dye, one can relate the dye signal to glucose concentration. The lifetime decay of the dye emission can be calculated and converted into an analyte concentration through an established calibration of lifetime decay values to analyte concentration. This analyte concentration value can be displayed to the end user. In order to measure concentrations of some analytes in the physiological range it can be advantageous to have appropriately sized reaction chambers such that the analyte will diffuse adequately into the sensor as to establish a concentration gradient within the sensor. With an excess of enzyme and short diffusional lengths the sensor response time can be very short.

A lactate sensor may also be fabricated in the same manner as the glucose sensor specifically by switching the enzyme glucose oxidase with lactate oxidase (or lactate oxidative decarboxylase, lactic oxygenase, lactate oxygenase, lactic oxidase, L-lactate monooxygenase, lactate monooxygenase and L-lactate-2-monooxygenase). The hydrogel then can contain lactate oxidase which can consume lactate and oxygen through the following reaction:

| Enzyme | Reaction |
|---|---|
| Lactate Oxidase (LOX): | L-Lactate + $O_2$ → pyruvate + $H_2O_2$ |

Enzymes other than glucose oxidase and lactate oxidase include hut are not limited to cholesterol oxidase, alcohol oxidase, bilirubin oxidase, ascorbate oxidase, choline oxidase, pyruvate oxidase, sarcosine oxidase, tyramine oxidase, Acyl-CoA oxidase and NADPH oxidase, and can be used to determine their respective analytes.

It will be understood that while enzymes are discussed above, different reactive/consuming/binding molecules can be used in their place. For example, DNA RNA, and chimeric aptamers can be used as the molecule. Further, the molecules can be those that consume, metabolize, or hind targets, such as analytes or oxygen. Accordingly, the molecules can include the enzymes disclosed herein (or other enzymes) that can metabolize any targets or analytes.

Dye

In some embodiments, light-sensitive reporting agents that can be used in the above-disclosed sensors can include porphyrin dyes (i.e. Platinum Tetrabenzo Porphyrin), and such porphyrin dyes may be used on or in the sensor, and the type of reporting agent is not limiting. Light can be emitted from a diode or other source and then absorbed by a light sensitive dye. The light-sensitive dye can be excited by the light source and the light-sensitive dye can emit light. Oxygen (or other targets) may bind to the light-sensitive dye thereby quenching light emission. The light emitted by the excited porphyrin dye can be collected on a photodetector and the intensity or decay time of the emitted light, is measured and can be related to the oxygen concentration through a known calibration. The probe can be used to continuously read the concentration of the analyte of interest over time, or it could be used to make intermittent measurements. The calculated concentration of analyte from the probe can be sent to a display where the user can interface with the device. In some embodiments, the oxygen (or other target) may not directly interact with the dye, and rather products of the reaction between certain molecules (such as the oxygen and analyte mediated by the enzymes disclosed above) can interact with the dye. For example, glucose and oxygen in the presence of glucose oxidase yields gluconic acid and hydrogen peroxide, and the concentration of hydrogen peroxide may be analyzed rather instead of or concurrently with the consumption of oxygen.

Following is a list of dyes that are sensitive to dissolved oxygen concentration, such as $CO_2$ and $O_2$, and which includes but is not limited to, metalloporphyrins such as PtOEP, PdOEP, PtTFPP, PdTFPP, PtOEPK, PdOEPK, PtIF-PPL, PdTFPPL, PtTPTBP, PdTPTBP, PtTPTBPF, PdTPT-BPF, Pt1NF, Pd1NF, Pt2NF, Pd2NF, Pt3NF, Pd3NF, PtTPTNP, PdTPTNP, PtTBP(CO2Bu)8, PdTBP(CO2Bu)8, PtNTBP, PdNTBP, Oxyphor R2, Oxyphor G2, PtTCPP. Additional dyes include but are not limited to cyclometallated complexes such as Ir(III) or Pt(II): Ir(ppy)3, Ir(ppy-NPh2)3, Ir(btpy)3. Additionally, transition metals polypyridyl complexes such as [Ru(bpy)3]2+, [Ru(dpp)3]2+ may also be used as dyes to measure dissolved oxygen concentration.

In a specific example, two different oxygen sensitive dyes may be used, one for the reaction chambers, and the other for the reference. The lactate-mediated $pO_2$ may be measured with a dye such as Platinum Tetra Phenyl Tetra Benzo Porphine (PtTPTBP) and the oxygen reference with a dye such as Platinum meso-tetra fluorophenyl porphyrin (PtTFPP). PtTPTBP is excited by red light and emits in the near infrared, while PtTFPP is excited by green light and emits in the red. Signals from these two dyes can be separated, for example, by their excitation and emission through the use of two different color LED's (red and green) and a dichroic beam splitter. In another specific example the reaction chambers and reference can be spatially separated and excited with separate light sources at distinct timepoints and the reaction chambers and reference can then use the same oxygen sensitive dye and the signals can still be separated. The signals from the reaction chambers and reference are separated by knowing which sensor was excited/probed at each time point.

An oxygen concentration reference measurement can be taken along with the measurement of analyte concentration in order to ensure that the analyte measurement value is not affected by changing oxygen levels. A second sensor with oxygen sensitive dye but no enzyme may be implanted in a separate site and the original or a second probe may be used to measure the oxygen value from that sensor to use as reference to the analyte sensor. This may not be the most accurate approach to obtaining a reference measurement, since the two sensors will be spatially separated and the oxygen levels in their respective environments may be different. In order to overcome this limitation, a second oxygen sensitive dye can be placed alongside the enzyme-coupled dye so that the second dye measures the oxygen level at the same implant site. The signals from the two dyes can be separated spectrally through emission filtering (i.e. PtTFPP and PtTPTBP) or by decay time, by choosing two dyes whose lifetime decay time ranges do not significantly overlap (i.e. PtTPTBP and PdTPTBP). PtTFPP has multiple absorption peaks at 390 nm, 504 nm and 538 nm. PtTFPP has an emission peak at 647 and 710 nm. PtTPTBP has multiple absorption peaks at 430 nm and 614 nm and an emission peak at 770 nm. PtTFPP can be excited by green light (~530 nm peak) and its emission can be collected through a bandpass filter that would exclude the excitation light and any emission from the PtTPTBP, while PtTPTBP can be excited by red light (~615 nm peak) and its emission can be collected through a bandpass or longpass filter that excludes the excitation light and any emission from PtTFPP. Decay times for PtTPTBP range from ~15-47 μs in vivo whereas PdTPTBP decay times range from ~70-286 μs in vivo. Since the decay times of PtTPTBP and PtTFPP do not overlap they can be separated.

System

In some embodiments, the sensor chip and probe may be able to display specific readouts. However, in some embodiments they can be incorporating into larger computing systems, such as a computer, laptop, tablet, smartphone, or video display, to name a few.

In some embodiments, specific analyte measurement readings can be outputted by the above devices. In some embodiments, the sensor may provide temporal trends in lactate, thus enabling the medical professional to tune a patient's therapies based on a patient's biological response to therapy. This real-time stream of information may facilitate incorporation of the data into central patient monitoring systems and enable a high degree of automation based on lactate trends, rates and magnitude. On the other hand, this sensor may be used individually on its own without connection to an entire patient monitoring system or an automated system that dispenses treatment to a patient.

Further, embodiments of the sensor may also act as a 'crash' alarm when a patient's lactate levels reach deleterious levels. Medical professionals can be notified by the 'crash' alarm of the patient's deleterious lactate levels, rate of change and history, and accordingly provide the medical attention required to stabilize the patient. Sensors can be set and used for other parameters, such as steep increases/decreases, or just general monitoring of analyte levels. The sensor may be implemented into a variety of patient monitoring systems and wirelessly provide notification of a patient's health to a medical professional.

In some embodiments, implanted portion of the sensor can have a width of about 200, 300, 400, 450, 500, 550, or 600 μm and a height of about 100, 200, 300, 400, 500, 530, 550, or 600 μm. In some embodiments, implanted portion of the sensor can have a width of less than about 200, 300, 400, 450, 500, 550, or 600 μm and a height of less than about 100, 200, 300, 400, 500, 530, 550, or 600 μm.

Method of Manufacturing

Example 1

Figure 13:
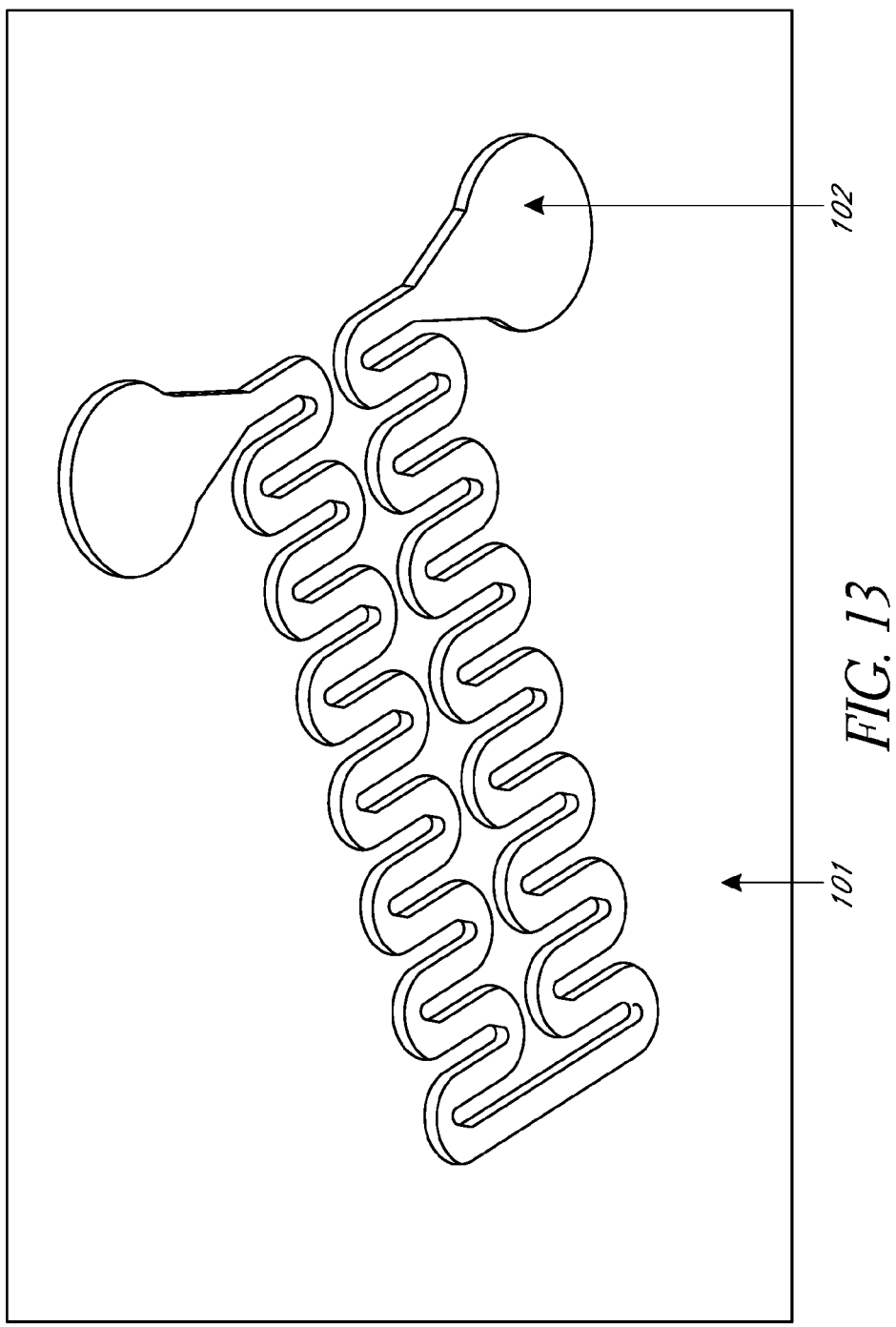
FIG. 13 illustrates a mold for an embodiment of a sensor that is formed out of SU-8.
Figure 14:
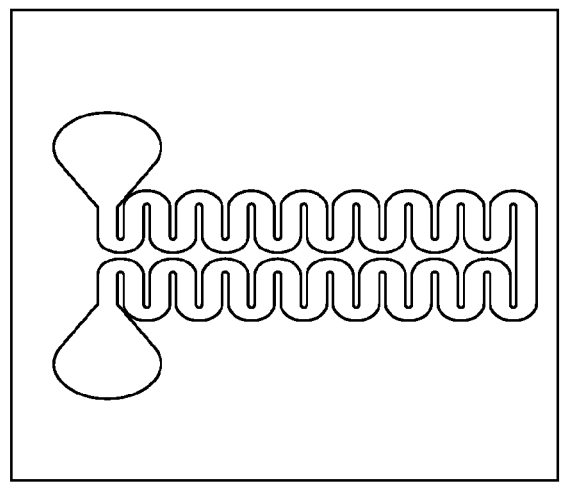
FIG. 14 illustrates the photo mask used to form the mold for an embodiment of sensor.
Figure 15:
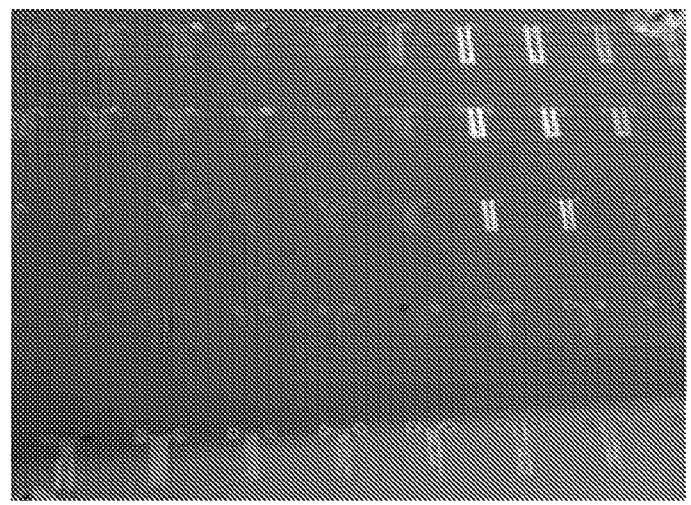
FIG. 15 illustrates how these molds may be multiplexed for manufacturing purposes.
Figure 16:
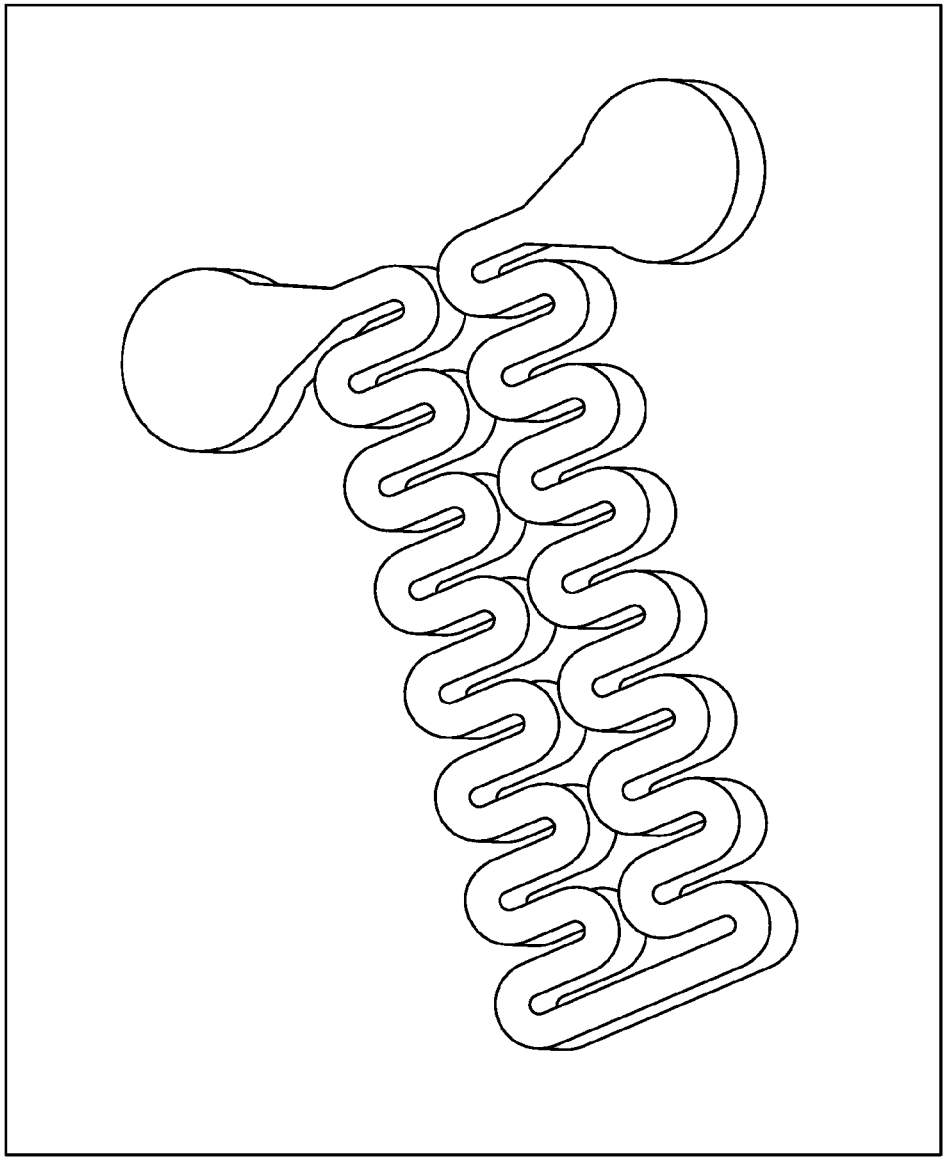
FIG. 16 illustrates an embodiment of a PDMS sheet with positive channels molded from the SU-8 mold.
Figure 17:
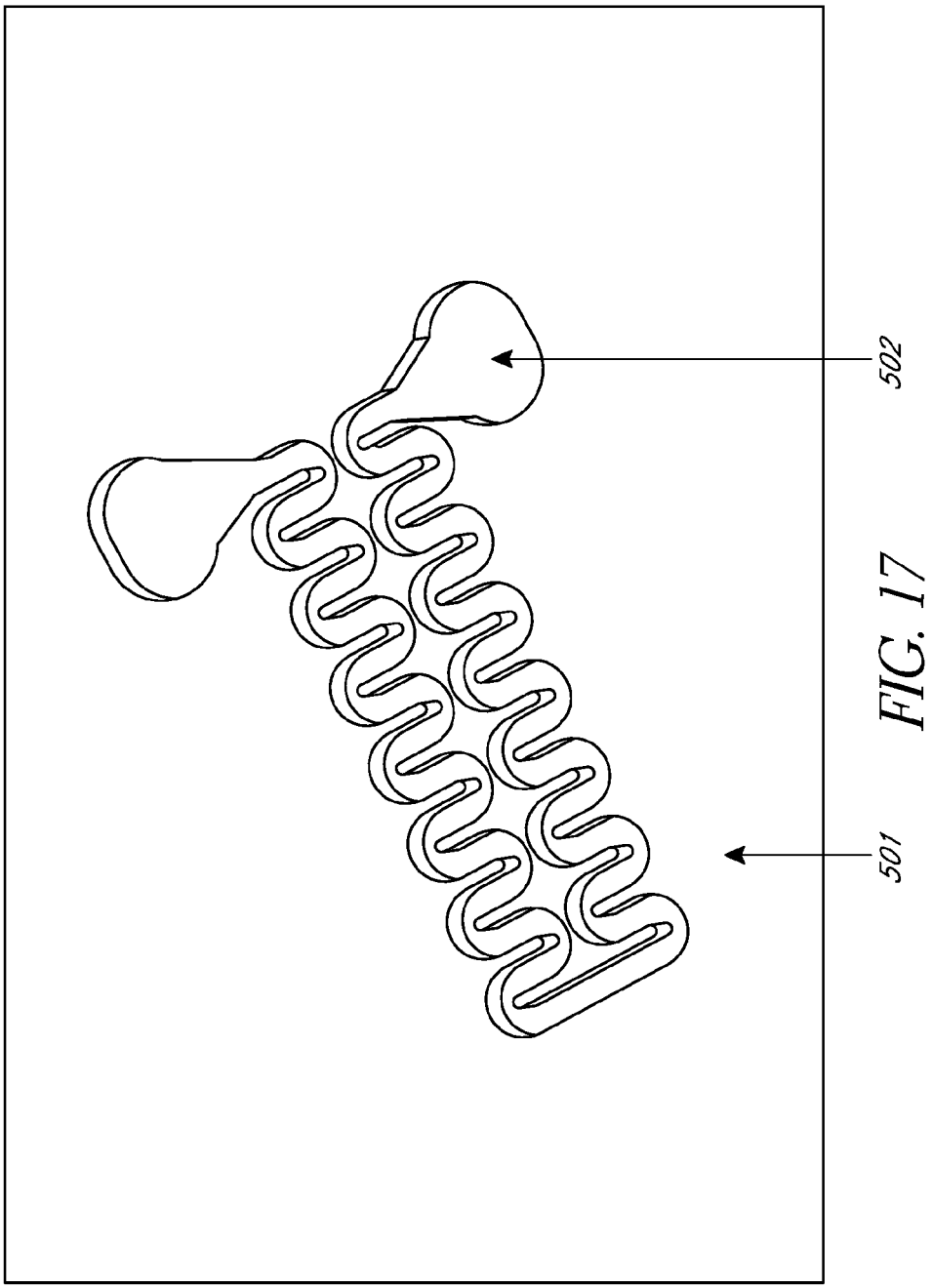
FIG. 17 illustrates an embodiment of a substrate for a sensor in which the dye and enzyme will be poured into the negative channels of the substrate.

Sensors can be manufactured but are not limited to the following description. A multitude of aforementioned sensor chips capable of measuring glucose and lactate may be fabricated as follows. First a mold can be formed out of SU-8 (101) on a wafer by photolithography (FIG. 13) with a patterned mask (FIG. 14). 102 are the negative features of the SU-8 wafer. The large cavities at the end of the channels can be used to more easily fill the cavities with a fluid (dye or unpolymerized hydrogel mixture). For filling, a drop of fluid can be placed in 102 and the cavity can be filled via capillary action. The mold can be generally serpentine, which can increase cavity filling efficiency, though the particular shape is not limiting. FIG. 15 shows how a significant number of these molds may be manufactured at one time. After the SU-8 mold is formed PDMS can be poured in a thin layer on top of the wafer and allowed to harden, forming a PDMS sheet with the sensor patterns and channels molded into it as shown in FIG. 16. Then a harder polymer that is less oxygen permeable can be molded off the PDMS mold by pouring a liquid polymer in a thin layer over the PDMS mold and allowing the harder polymer to cure (i.e. air cure, UV cure, heat cure, etc.) (FIG. 17). 501 is the harder polymer and 502 is the negative channel. The harder polymer that is molded off the PDMS mold may include but are not limited by the following materials such as acrylate, polymethylmethacrylate (PMMA), diverse epoxies, Mylar, polyethylene, PET, PTFE, and polyamides. In order to make negative features (channels) for the sensor the SU-8 mold can be a negative mold that the PDMS flows into to form a positive mold that will create the final negative channel features in the harder and less oxygen permeable sensor material.

The mold can be formed such that the dye and enzyme can be loaded into all of the reaction chambers simultaneously. Dye can be coated onto the bottom of a series of interconnected channels that were formed in the molded polymer. It can be coated all at once by placing a drop of dye solution (dye solution may comprise the following: 2 mg PtTPTBP and 30 mg polystyrene dissolved in 450 μl chloroform) on an inlet (502) that wicks the dye dissolved in a solvent into the channels via capillary action where it dries, forming a thin, solid layer. The enzyme mixture, which may contain, but is not limited to, an oxidase enzyme (such as glucose oxidase), serum albumin, water, PEG, HEMA, alginate, cellulose acetate, etc., can then be loaded on top of the dye and polymerized so that it remains in contact with the dye.

Example 2

In some embodiments, the dye can be incorporated into the enzyme hydrogel mix. This can be accomplished by breaking up the dye particles into small pieces (1 micron-20 micron, for example) and mixing them into the liquid enzyme pre-gel solution; the dye particles can become trapped in the gel upon hardening (trapped because the pore size of the gel is much smaller than the dye particles).

2 mgs of dye can be mixed with 30 mgs of polystyrene and dissolved in 450 μL of chloroform. A thin sheet of the dye and polystyrene can be formed by pipetting the dye and polystyrene solution onto a glass slide and the chloroform is allowed to evaporate overnight. A razor can then be used to break the thin dye layer up into fine particles and the particles can be further ground with a mortar and pestle. These particles can be taken up in solution with hydroxyethylmethacrylate (HEMA) at 0.1 wt %, polyethyleneglycol (PEG) at 0.9 wt % and water. The mixture can then be mixed with a vortex mixer to disperse the particles evenly throughout the liquid. The resulting mixture can be pipetted over the top of all the channels allowing it to fill the channels and the excess fluid over the top of the channels was siphoned off with a pipette. In some embodiments, this can leave only the fluid filling the channels into the loading chamber of the sensor and the mixture was wicked into the sensor's channels.

Another embodiment to create an integrated dye and enzyme reaction chamber is choosing a water soluble dye particle (e.g. Oxyphor G2) and functionalizing the dye particles with chemical groups that covalently bind with other functional groups of the enzyme gel mixture. For example, if Oxyphor G2 was functionalized with amine groups, then those dye particles would be able to covalently attach to albumin, enzymes, or other proteins present in the enzyme gel. In this case the dye particles can be mixed throughout the liquid enzyme pre-gel solution and they can stay in the enzyme gel upon hardening and through washing due to their covalent attachment. Water soluble dye particles without any functional groups to provide covalent attachment can leach out of the gel over time because the dye particles are smaller than the pore size of the hydrogel containing enzyme.

The exposed top of the sensor can then be coated immediately with a thin layer of a polymer (e.g. silicone) that can be impermeable to the analyte, but permeable to oxygen as to reduce the likelihood of the reaction within the sensor becoming oxygen-limited. Once this layer has polymerized the sides of the channels can be cut away, exposing the reaction chambers (601) to fluid containing the analyte as shown in FIG. 1. 602 is the other polymer that has been molded from the PDMS mold and may be harder and/or impermeable to oxygen and 603 is the thin layer silicone that was coated on top of the sensor.

Identifying Location of Implanted Sensor

As mentioned above, the sensor chip can be implanted into a patient. It can then be advantageous for a probe to be located approximately over the sensor chip. Several methods may be used to determine the location of the sensor following implantation. For convenience, these methods may be performed by the same probe system used to interact with and collect data from the sensor. Each can be performed by moving the detection system around the approximate location of the sensor until a given condition is met. Once this condition is met, the current location of the detection system can be used for further data acquisition from the sensor.

These methods include first optical detection of the luminescent signal from the dye within the sensor. By continually pulsing an optical excitation source and using the onboard photodetector and accompanying hardware, the presence or lack of luminescent decay following the light pulses may be used to indicate the presence of the sensor below the detection system. This process is aided by the fact that any intrinsic luminescent species within tissue that absorbs light of the same wavelengths as the excitation light source has lower emission intensity as compared to the emission intensity of the sensor dyes. In some embodiments, data collected using the photodetection system following each excitation pulse can be analyzed to determine whether a given signal intensity is reached or whether a mathematical fit to the collected data reaches a specific goodness of fit. If one or either of these conditions are met, the detection system can inform the user that the sensor has been found.

In some embodiments, inclusion of a fluorescent species within the sensor can be used. The detection system may use onboard light sources to optically excite the fluorescent species through the skin while simultaneously monitoring the intensity of any detected fluorescence using the photodetector and accompanying hardware. If a fluorescence signal of an adequate intensity is detected, the detection system can inform the user that the sensor has been found.

In some embodiments, a reflective element within the sensor can be added such that light impinging upon the sensor will be reflected. In this manner, light emitted from the detection system can be reflected at a higher intensity when the detection system is placed proximal to the sensor because the sensor increase the amount of reflected light that would be provided by tissue alone. A threshold can therefore be set for the intensity of reflected light detected by the photodector and accompanying hardware. Once this threshold is reached, the detection system can inform the user that the sensor has been found.

In some embodiments, a magnetic element can be added to the embedded sensor. A magnetometer can then added to the detection system. The detection system can then be moved around the approximate location of the sensor until an appropriately high signal is recorded by the magnetometer, indicative of the sensor being present beneath the detection system. Alternatively, magnetic species may be placed in both the detector and the sensor so that magnetic attraction between these two bodies can felt by the user. Once this attraction is felt, the user will be aware that the detection system is located adequately close to the sensor.

In some embodiments, a compact radio-frequency identification (RFID) chip can be included within the sensor. The detection system would then include the hardware necessary to detect the presence of the RFID chip. The detection system can then be moved around the approximate location of the sensor until an appropriately high signal is recorded by the RFID detection hardware, indicative of the sensor being present beneath the detection system.

In some embodiments, an electronically conductive element can be included, including but not limited to, a loop of conductive wire, within the sensor. The detection system would then include the hardware necessary to detect the presence of this electronically conductive element within the sensor. The included hardware is colloquially known as a metal detector, and may potentially utilize very low frequency, pulse induction, and beat-frequency oscillation techniques to detect the sensor. The detection system can be moved around the approximate location of the sensor until an appropriately high signal is recorded by the metal detection hardware, indicative of the sensor being present beneath the detection system.

If a light source is included with the sensor as described above, the presence of light from beneath the tissue (be it excitation light from the light source or emission light from the sensor) may be used for sensor localization.

In Vitro Lactate Calibrations with Sensor

Figure 18:
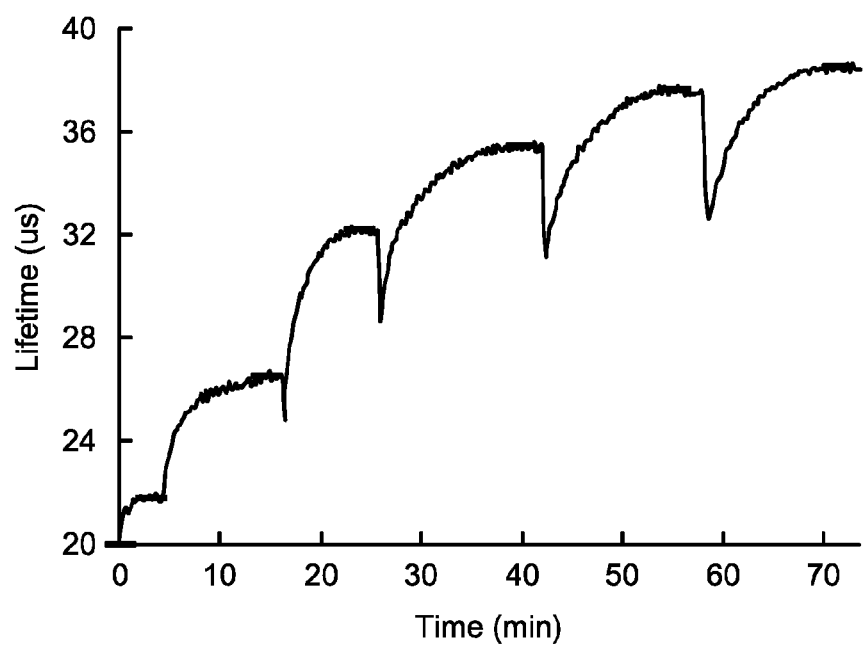
FIG. 18 is a graph detailing lactate sensor luminescence lifetime measurements obtained from an embodiment of a lactate sensor.
Figure 19:
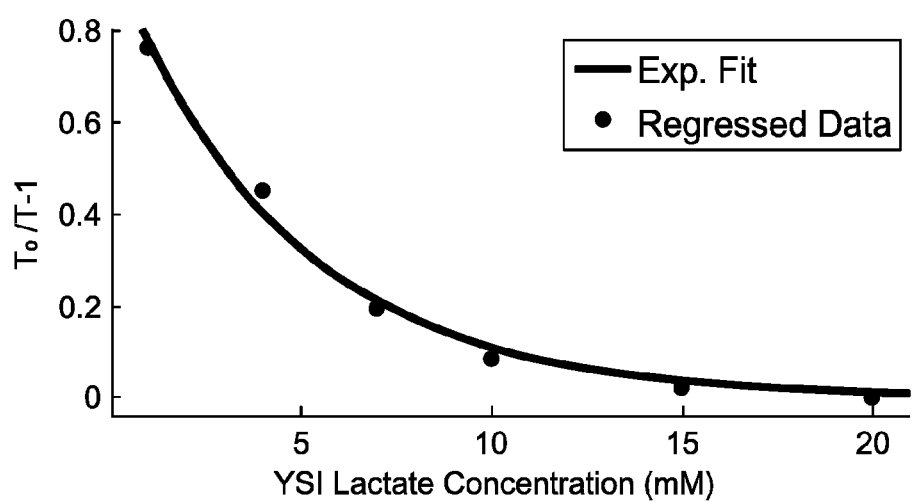
FIG. 19 is a graph detailing transformed in vitro lactate sensor luminescence lifetime measurements compared to measurements from a commercial YSI 2300 STAT Plus analyzer.

95% of 41 manufactured sensors showed in vitro sensitivity to lactate across clinical concentrations. CLM sensitivity was quantified by placing the device in a single well of a 24 well plate, and pipetting in a sequence of solutions of increasing lactate concentration. Luminescence lifetime (T) of the oxygen sensitive dye was measured every 10 seconds. With each fluid exchange T rises exponentially in time to reach a new steady state specific to that concentration (FIG. 18). The lactate concentration of each solution is independently measured by a gold standard YSI 2300 STAT Plus analyzer. Steady state values of T are transformed by the equation $T0/T-1$, where T0 is the lifetime constant for $pO2=0$. $T0/T-1$ is regressed against YSI measurements to formulate a calibration curve as shown in FIG. 19. It was found that calibration followed a negative exponential relationship with R2 of >0.99.

Testing Results

Different testing experiments were used to determine the viability of embodiments of the disclosed sensor.

In Vivo Lactate Measurements Using an Implanted Sensor

In order to validate that the sensor works when implanted in the subcutaneous space, a rabbit model of cyanide poisoning and recovery was used. During cyanide poisoning, lactate levels rise due to the inability of cells to undergo cellular respiration through oxidative phosphorylation. This necessitates increased anaerobic metabolism in vital systems and a resulting pathological increase in systemic lactate concentration. Rising lactate concentration causes acidosis-mediated shock, multi-organ failure and acute danger of death. Such anaerobic lactate production is common in critical medical conditions including hemorrhage, sepsis, and pulmonary injury with hypoxemia. Importantly, rising lactate concentration correlates closely with extent of injury and effectiveness of resuscitative treatments.

By tracking the rise in lactate it was verified that the implanted sensor tracks the lactate values throughout the clinical range when compared to blood lactate measurements taken by commercial analysis devices.

First, a patterned lactate sensor (without an oxygen reference) was implanted into a rabbit and cyanide was administered to the rabbit. Then a lactate sensor and an oxygen reference sensor was implanted into a different rabbit and administered cyanide poisoning and an antidote to promote recovery. In both experiments the implanted sensors signals correlate strongly with blood lactate measurements from commercial devices.

In the second experiment, during the recovery phase when the lactate levels begin to decrease after the rise, the implanted sensor signal reports falling lactate levels over 20 minutes before the blood lactate measurements. This may be explained as follows. The implanted sensor is in the interstitial fluid of the rabbit tissue. Lactate is produced in tissue and a large portion of that lactate then diffuses into the bloodstream and passes through the liver where lactate is consumed. When the rabbit is poisoned with cyanide, its rate of lactate production is higher than its liver's rate of lactate consumption, so the lactate levels increase. When the rabbit is recovering, lactate production in tissue decreases to the point that the rate of lactate production is lower than the liver's rate of lactate consumption and lactate levels begin to decrease. This decrease happens in the tissue before the blood as tissue lactate production is slowed and the leftover lactate continues to diffuse into the blood stream.

This ability of embodiments of the sensor to detect falling lactate levels before blood lactate measurements would provide earlier indications of a patient's condition to a physician that could be used to make treatment decisions.

Figure 20:
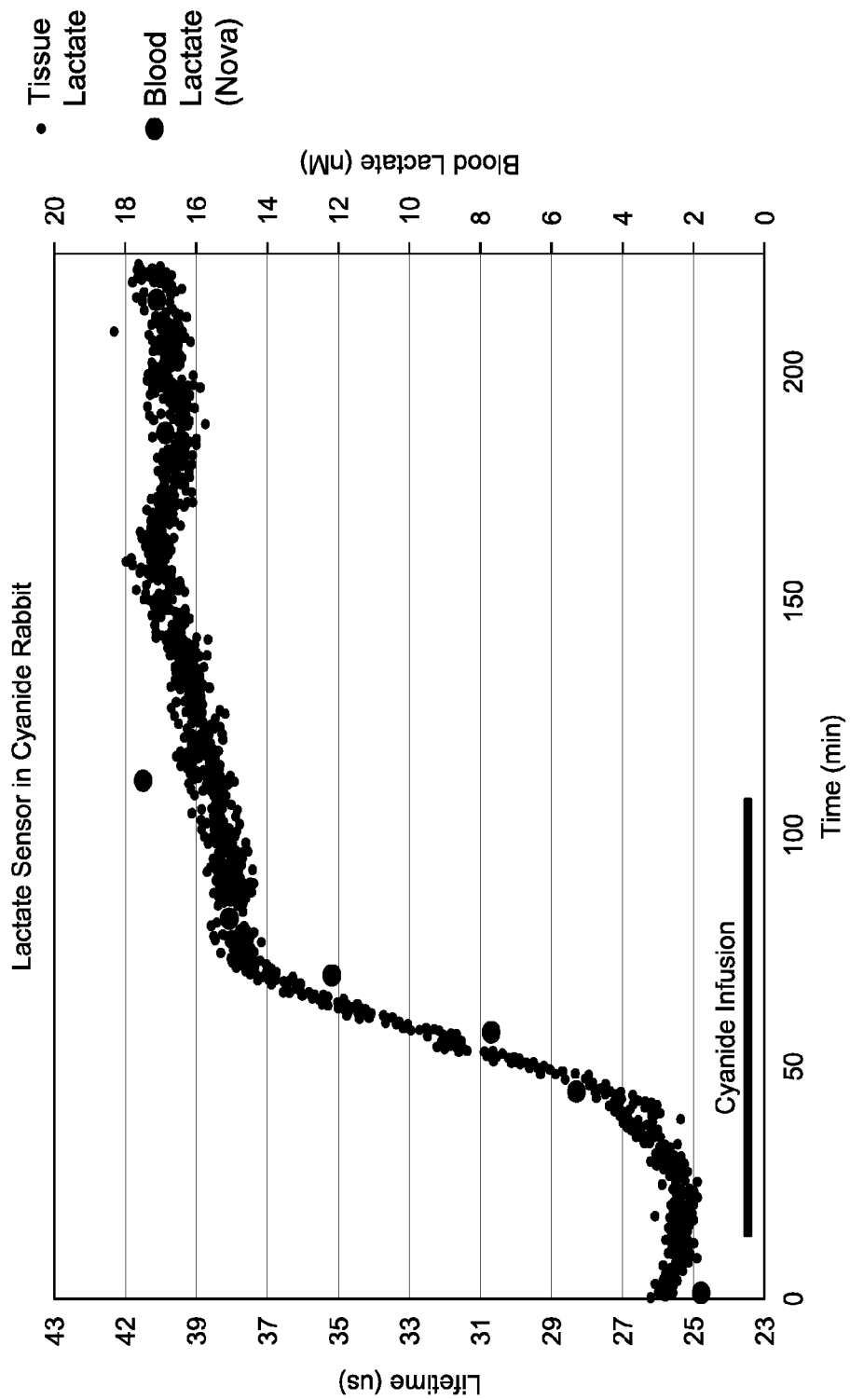
FIG. 20 is a graph detailing in vivo lactate measurements obtained from an embodiment of a lactate sensor implanted into a rabbit model of cyanide poisoning.

FIG. 20 shows the measurements obtained from embodiments of a lactate sensor implanted subcutaneously (~2 mm below skin surface) in an anesthetized rabbit and the wound was sealed. Embodiments of the excitation and detection probe were aligned with the sensor and lifetime measurements of the dye in the sensor were recorded every 10 seconds. Arterial blood was drawn at specific time points to compare to the implanted sensor values. After cyanide infusion begins, the lactate levels begin rising in the blood and our sensor lifetime begins rising as well, as expected. A retrospective alignment of the implanted sensor signal and the blood lactate measurements show a strong correlation between our sensor and the measurements made with a Lactate Plus commercial blood lactate meter made by Nova Biomedical.

Figure 21:
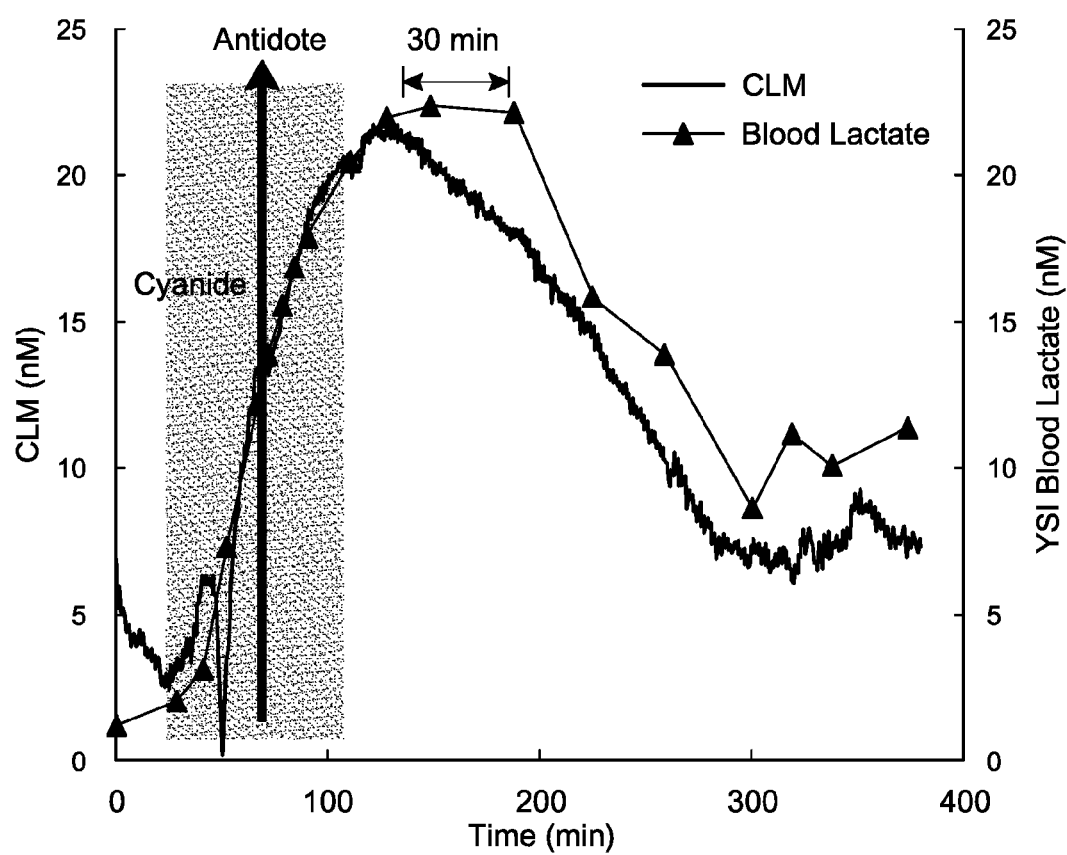
FIG. 21 is a graph detailing the in vivo lactate measurements obtained from an embodiment of a lactate sensor implanted into a rabbit model of cyanide poisoning in which the rabbit received an antidote.

FIG. 21 shows the measurements obtained from an embodiment of a lactate sensor that was implanted subcutaneously (~2 mm below skin surface) in an anesthetized rabbit and an oxygen sensor was also implanted to provide a reference signal, separate excitation/detection probes were aligned with the sensors and lifetime measurements of the dye in the sensors were recorded every 10 seconds. The oxygen sensor used as the reference was made in a similar manner as the sensors described in Examples 2 and 3. Arterial blood was drawn at specific time points and its lactate levels were measured with a commercial lactate analyzer (YSI 2300) to compare to the implanted sensor values. A retrospective alignment of the implanted sensor signal minus the oxygen reference signal and the YSI blood lactate measurements show a strong correlation between our sensor and the commercial blood lactate meter as lactate rises following cyanide infusion. At approximately 50 minutes after the injection of an antidote, the sensor reports falling lactate concentration and thus the antidote is an effective treatment. The blood does not report the fall in lactate until at least 80 minutes post injection, showing that the sensor would inform clinical staff of a positive therapeutic response as much as 30 minutes before the blood. Clinical blood draws are taken intermittently at irregular times and the time delay between the blood draw and the sensor contemplated within would likely be longer. Additionally, the sensor can be engineered and programmed to autonomously alert the medical professionals to the initiation of recovery, thus providing a hands-free monitor to complement pulse oximetry and ECG.

Figure 22:
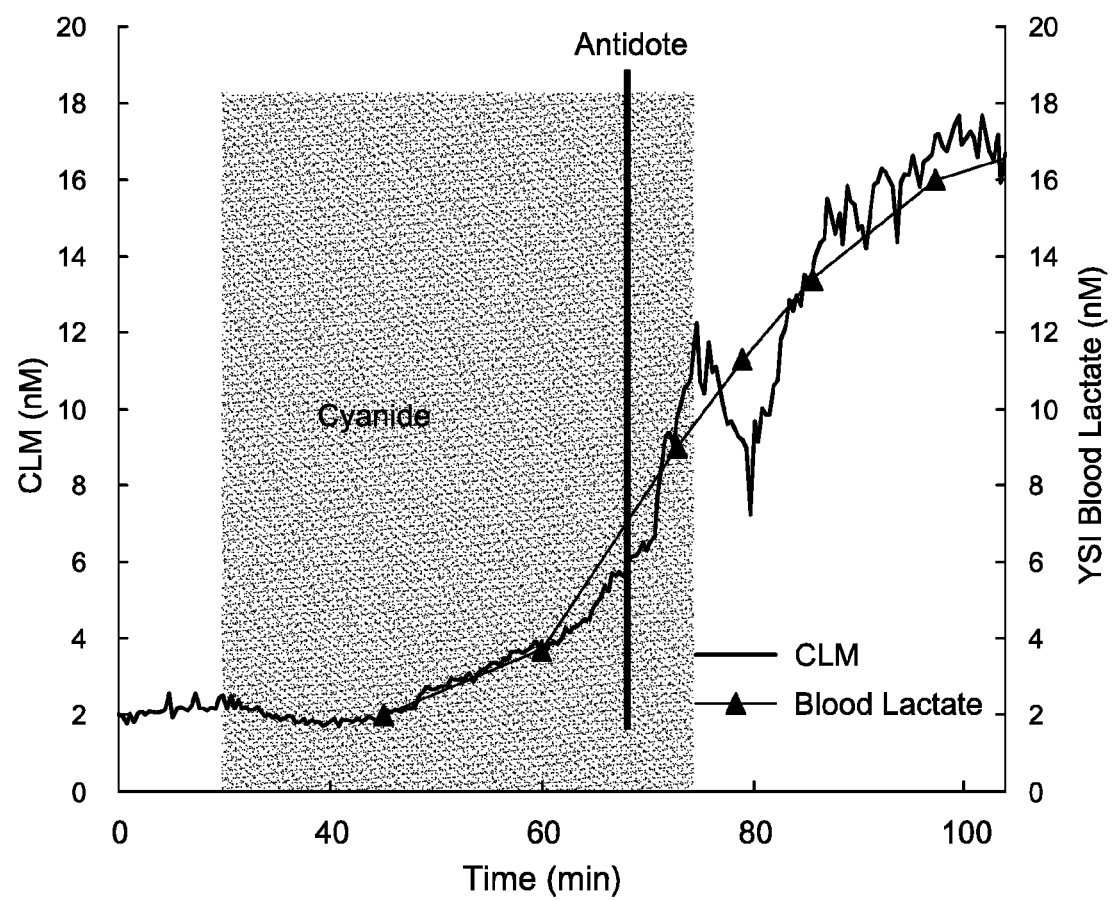
FIG. 22 is a graph that tracks the lactate levels of a rabbit where the rabbit did not recover from cyanide poisoning.
Figure 23:
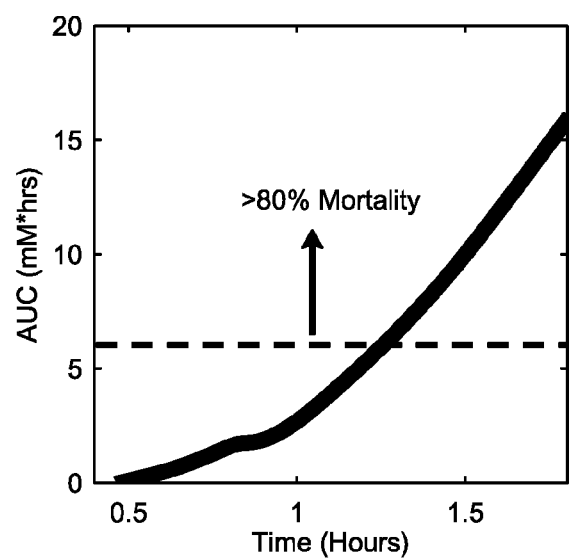
FIG. 23 is a graph detailing that the area under the curve (AUC) may be measured with an embodiment of a lactate sensor.

All 13 of the tested lactate sensors successfully tracked blood lactate. A typical experiment in Which the rabbit did not survive cyanide poisoning is shown in FIG. 22. The putative antidote was ineffective in this animal leading to fatal levels of lactate followed by a severe drop in blood pressure, which according to protocol necessitated the animal to be sacrificed. The grayed region indicates duration of cyanide infusion, which was stopped approximately ten minutes after antidote injection. Results show the sensor tracked blood lactate with no delay as it rose from approximately 0.5 mM to in excess of 16 mM lactate. Unlike the intermittent blood measurements, the sensor allows for calculation of Area Under the Lactate Concentration Curve (AUC, FIG. 23), shown clinically to indicate early resuscitation. It has been shown that an AUC>6 mM*hrs correlates with a greater than 80% rate of mortality. The sensor detected AUC crossing threshold of >6 mM*hrs and the animal did not recover.

In another experiment, an embodiment of the above described lactate sensor and reference oxygen sensor attached to LED's were implanted in rabbit skin with a detector placed on top of skin above the implanted sensor. The experiment again involved rabbit cyanide poisoning and tracking lactate levels in rabbit tissue and comparing to blood lactate over course of experiment. At minute 25, a lethal cyanide dose was given orally and lactate values subsequently rise in the tissue (as measured by the implanted sensor) and in the blood (as measured by a YSI 2300 lactate analyzer). Implanted sensor lactate values were obtained from subtraction of the reference oxygen sensor response from the lactate sensor response.

Figure 24:
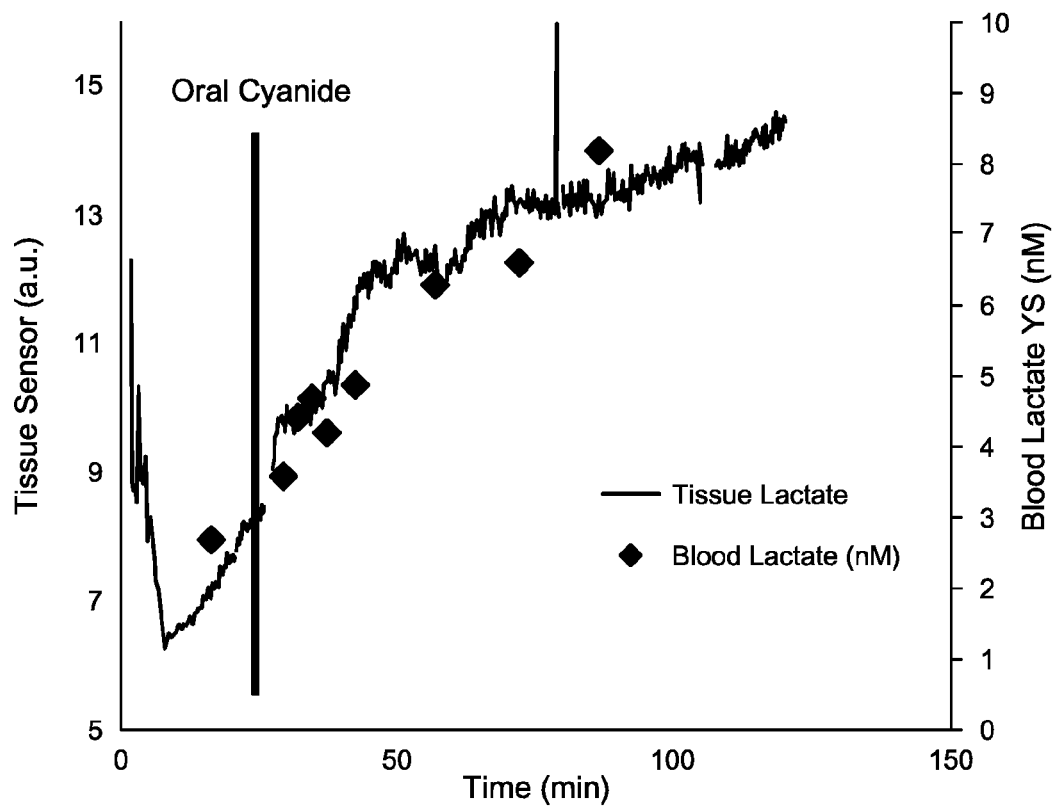
FIG. 24 illustrates testing results of embodiment of an LED sensor in rabbit tissue.

In a rabbit model of cyanide poisoning, the sensor response to lactate correlates well with blood lactate measurements taken over the course of the experiment, as shown in FIG. 24.

In Vivo Glucose Measurements Using an Implanted Sensor

Figure 25:
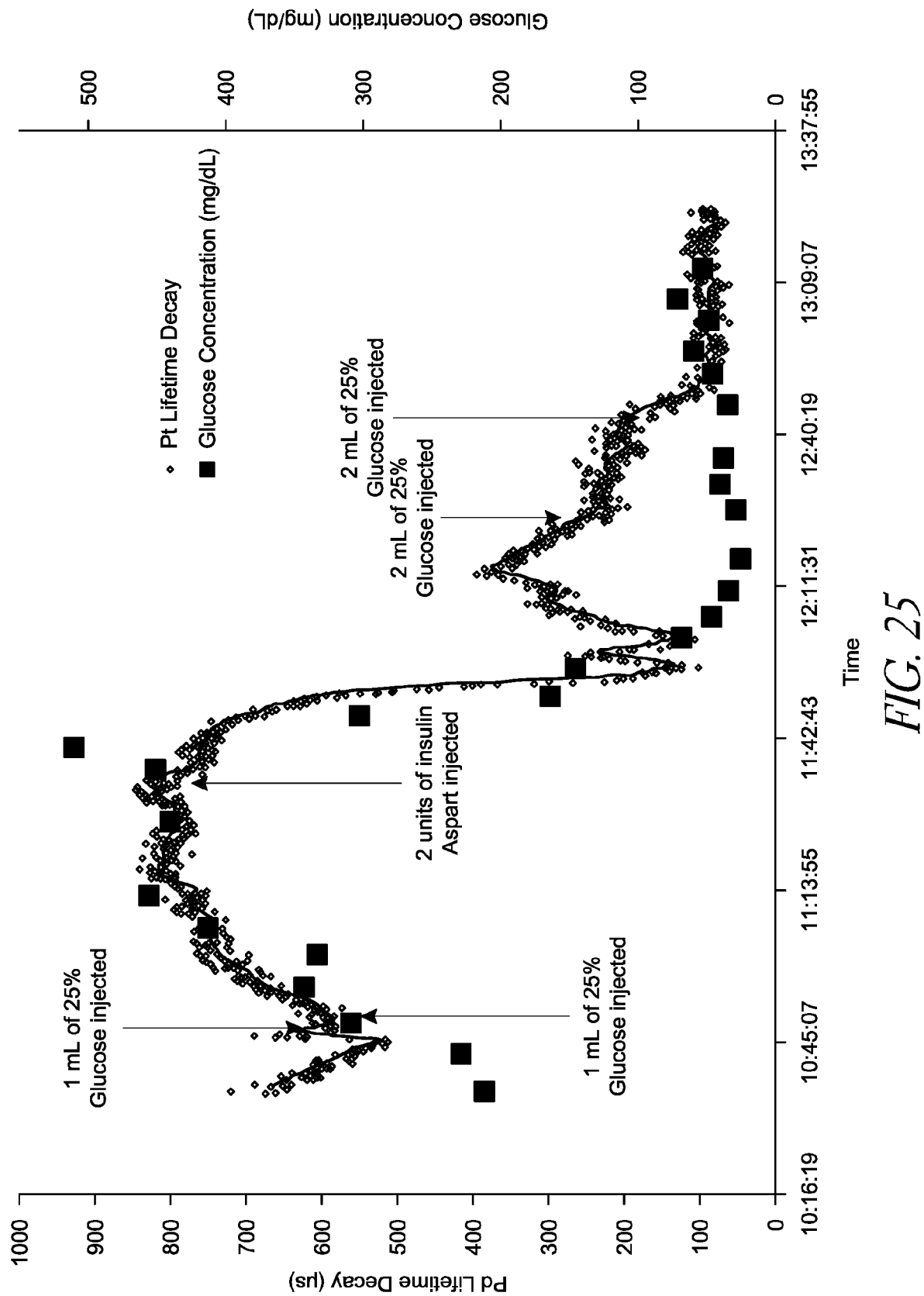
FIG. 25 is a graph detailing the in vivo glucose measurements obtained from an embodiment of a glucose sensor implanted into a rat model.

FIG. 25 shows the measurements obtained from an embodiment of a glucose sensor that was implanted subcutaneously (~2 mm below skin surface) in an anesthetized diabetic rat with the wound sealed. A probe was aligned with the implanted sensor and lifetime measurements of the dye in the sensor were recorded every 10 seconds. Tail vein blood was sampled at specific time points to compare to the implanted sensor values. After glucose is injected the glucose levels begin rising in the blood and the sensor lifetime begins rising too. A retrospective alignment of the implanted sensor signal and the blood lactate measurements show a strong correlation between our sensor and the commercial blood glucose meter. The commercial blood glucose meter used is the Bayer Contour, a finger stick blood draw device. Blood was drawn from the rat's tail and the Bayer Contour read the glucose levels in the rat's blood.

Figure 26:
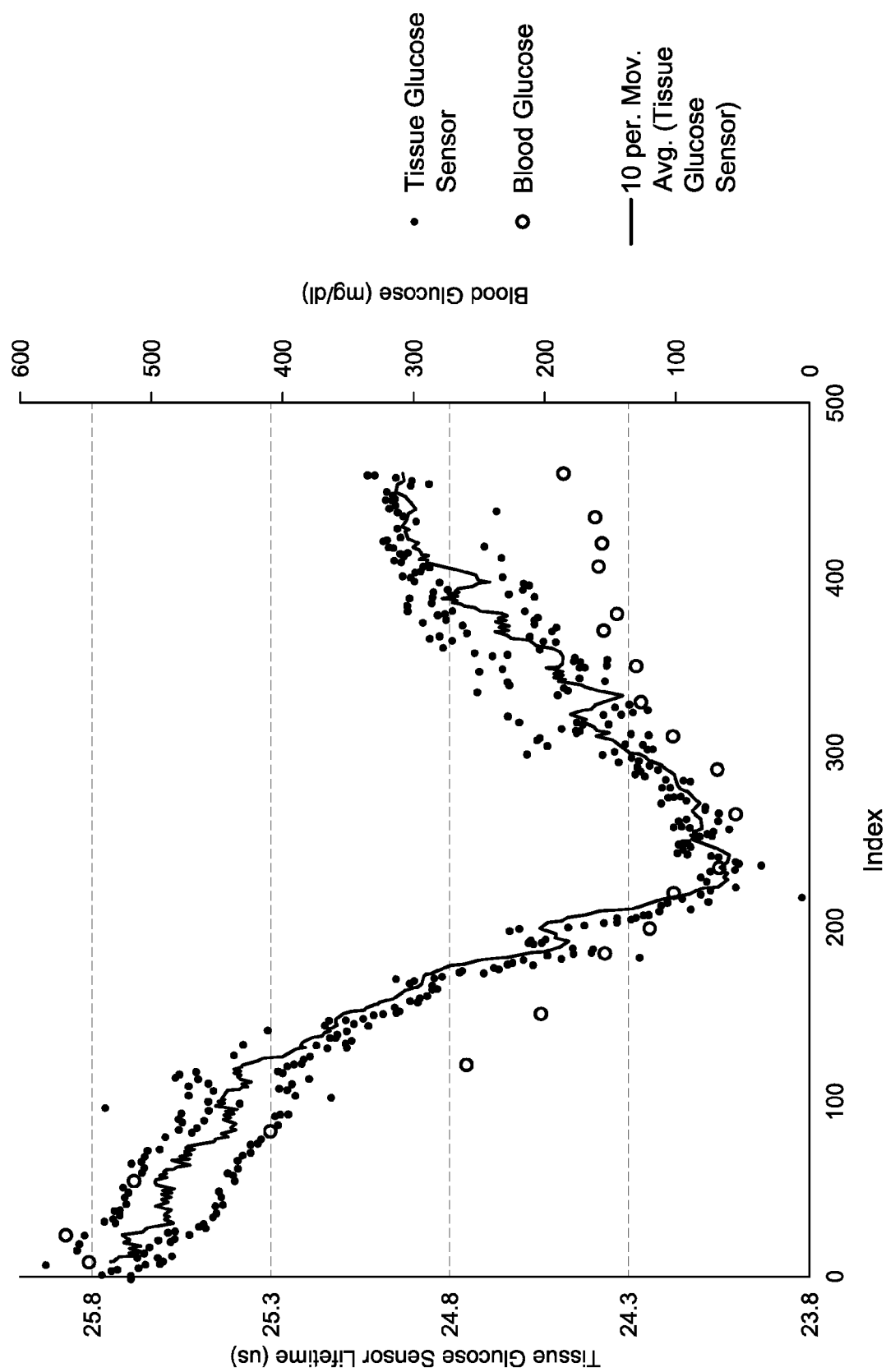
FIG. 26 is a graph detailing the in vivo glucose measurements obtained from an embodiment of a glucose sensor implanted into a rat model.

FIG. 26 shows the measurements obtained from a glucose sensor that was implanted subcutaneously (~2 mm below skin surface) in an anesthetized rat with the wound sealed.

A probe was aligned with the sensor and lifetime measurements of the dye in the sensor were recorded every 10 seconds. Tail vein blood was sampled at specific time points to compare to the implanted sensor values. After insulin is injected the glucose levels begin falling in the blood and our sensor lifetime begins falling as well, as expected. A retrospective alignment of the implanted sensor signal and the blood glucose measurements show a strong correlation between our sensor and the above mentioned commercial blood glucose meter.

From the foregoing description, it will be appreciated that an inventive product and approaches for analyte sensors are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1 of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

REFERENCES

Brohi K, Levy H, Boffard K, Riau B, Kiepert P, Zielske D. 643: Normalization of Lactate Within 8 Hours or a 20% Clearance in Initial 2 Hours Correlates With Outcomes From Traumatic Hemorrhagic Shock. Critical Care Medicine. 2011:39(12):177.

Graham D L, Laman D, Theodore J and Robin E D 1977 Acute cyanide poisoning complicated by lactic acidosis and pulmonary edema Arch. Int. Med. 137 1051-5

Stekelenburg A, Gawlitta D, Bader D L, Oomens C W. Deep tissue injury: how deep is our understanding? Archives of physical medicine and rehabilitation. 2008; 89(7): 1410-3.

Hosogai N, Fukuhara A, Oshima K, Miyata Y, Tanaka 5, Segawa K, Furukawa S, Tochino Y, Komuro R, Matsuda M. Adipose tissue hypoxia in obesity and its impact on adipocytokine dysregulation. Diabetes. 2007; 56(4):901-11.

Guiseppi-Elie A, Brahim S, Wilson A (2006) Biosensors based on electrically conducting polymers. In: Skotheim T, Reynolds J R (eds) Handbook of conducting polymers: conjugated polymer processing and applications, 3rd edn. Marcel Dekker, New York, pp 435-479

Edgar C E (2009) Baghdad ER revisited: The 28th Combat Support Hospital of Operation Iraqi Freedom 2006-2008. In: Tountas K H (ed) Third Military Health Research Forum (MHRF). Hallmark Crown Center, Kansas City, Mo., USA Sambasivan C N, Schreiber M A (2009) Emerging therapies in traumatic hemorrhage control. Curr Opin Crit Care 15:560-568

Bakker J, Gris P, Coffernils M, Kahn R J, Vincent J L (1996) Serial blood lactate levels can predict the development of multiple organ failure following septic shock. Am J Surg 171:221-226

Nguyen H B, Rivers E P, Knoblich B P, Jacobsen G, Muzzin A, Ressler J A, Tomlanovich M C (2004) Early lactate clearance is associated with improved outcome in severe sepsis and septic shock. Crit Care Med 32:1637-1642

Jansen T C, van Bommel J, Bakker J Crit Care Med. 2009 October; 37(10):2827-39.

Jones A E, Shapiro N I, Trzeciak S, Arnold R C, Claremont H A, Kline J A: Lactate clearance vs central venous oxygen saturation as goals of early sepsis therapy: a randomized clinical trial. JAMA 2010, 303(8):739-746.

Jansen T C, van Bommel J, Schoonderbeek F J, Sleeswijk Visser S J, van der Klooster J M, Lima A P, Willemsen S P, Bakker J: Early lactate-guided therapy in intensive care unit patients: a multicenter, open-label, randomized controlled trial. Am J Respir Crit Care Med 2010, 182(6): 752-761.

Angus D C, Linde-Zwirble W T, Lidicker J, Clermont G, Carcillo J, Pinsky M R, Crit. Care Med. 2001; 29(7): 1303-1310.

Rivers E P, Nguyen B, Haystad S, et al. Early goal-directed therapy in the treatment of severe sepsis and septic shock. N Engl J Med. 2001; 345(19):1368-1377.

De Backer D., *Lactic acidosis*. Intensive Care Med. 2003 May; 29(5):699-702. Epub 2003 Apr. 8.

Bakker J, Gris P, Coffernils M, Kahn R J, Vincent J L. Am J Surg. 1996; 3(2):221-226. doi: 10.1016/S0002-9610(97) 89552-9.

Aufderheide, Tom P., and, Keith G. Lurie. "Death by hyperventilation: a common and life-threatening problem during cardiopulmontny resuscitation." *Critical care medicine* 32.9 (2004): S345-S351.

N. E. Madias, Kidney Int., 29 (1986) 752, Animal Studies

Z. Mavric, L. Zaputovic, D. Zagar, A. Matana and D. Smokvina, Am. J. Cardiol., 67 (1991) 565.

P. B. Oliver, Am. J. Med., 48 (1970) 209.

J. L. Vincent, P. Dufaye, J. Berre, M. Leeman, P. J. Degaute and R. Kahn, Crit. Care Med., 11 (1983) 449.

B. N. Cowan, H. J. G. Bums, P. Boyle and I. McA. Ledingham, Anaesthesia, 39fl984) 750.

http://dx.doi.org/10.1186%2F2110-5820-3-12.

Vanni, Simone et al *Annals of emergency medicine* (2013).

V. Vitek, and R. A, Cowley, *Annals of surgery* 173.2 (1971): 308.

Hashimoto, Makoto, et al. *Surgery today* 43.2 (2013): 136-140.

van Everdinge, K. J., et al. *Annals of neurology* 442 (1998): 167-176.

Gonzalez, M. J., et al. *European Heart Journal* 34.suppl 1 (2013): P1518.

Adrie, Christophe, et al. *Circulation* 106.5 (2002): 562-568.

Mikkelsen Mark E., et al. *Shock* (Augusta, Ga.) (2013).

Kottmann, Robert Matthew, et al. *American journal of respiratory and critical care medicine* 186.8 (2012).

Manikis, Panagiotis, et al. *The American journal of emergency medicine* 13.6 (1995): 619-622.

Bakker J, Gris P, Coffernils M, Kahn R J, Vincent J L. Am J Surg. 1996:3(2):221-226. doi: 10.1016/S0002-9610(97) 89552-9.

Jansen T C, van Bommel J, Woodward R, Mulder P G, Bakker J. Crit. Care Med. 2009; 3(8):2369-2374. doi: 10.1097/CCM.0b013e3181a0f919.

Angus D C, Linde-Zwirble W T, Lidicker J, Clermont G, Carcillo J, Pinsky M R,

Crit Care Med, 2001; 29(7):1303-1310.

Sharman, Kristin K., et al. "Error analysis of the rapid lifetime determination method for double-exponential decays and new windowing schemes." *Analytical chemistry* 71.5 (1999): 947-952.

Collier, Bradley B., and M. Meshane. "Temperature Compensation of Oxygen Sensing Films Utilizing a Dynamic Dual Lifetime Calculation Technique." 1-1. SPIE BiOS 2013.

All of the above listed references are hereby incorporated by reference in their entirety.

What is claimed is:

1. A sensing method comprising:
   inserting at least a first light source and sensor pair and a second light source and sensor pair into a patient, wherein the first light source and sensor pair includes a first light source and a first sensor and the second light source and sensor pair includes a second light source that is different from the first light source and a second sensor that is different from the first sensor, each of the first sensor and the second sensor comprising one or more reaction chambers, each reaction chamber having a luminescent dye configured to interact with a target and generate a luminescent signal, wherein changes in signal are related to a concentration of the target, a molecule that interacts with the target during a breakdown of an analyte, and the analyte, wherein the luminescent dye, molecule, and analyte are proximal to one another, wherein each light source and sensor pair is configured to analyze one analyte;
   applying a probe onto a skin of the patient over the first light source and sensor pair and the second light source and sensor pair;
   temporally separating illumination of the first light source to irradiate the first sensor so that the luminescent dye in each reaction chamber of the first sensor produces a luminescence from illumination of the second light source to irradiate the second sensor so that luminescent dye in each reaction chamber of the second sensor produces a luminescence; and
   detecting the luminescence associated with luminescent dye of each reaction chamber of the first sensor and the second sensor by the probe to determine levels of the analyte.

2. The method of claim 1, wherein the luminescence exits the patient through the skin.

3. The method of claim 1 or 2, wherein the changes in signal are the changes in the intensity or lifetime of the signal.

4. The method of claim 1 or 2, wherein a lifetime of the luminescence is detected.

5. The method of claim 1, wherein a wire or a multitude of wires is connected to each of the first light source and the second light source to power the light sources.

6. The method of claim 5, wherein a portion of the wire or multitude of wires are implanted into the patient, wherein the wire or multitude of wires is utilized as a tether for retrieval of the first light source and sensor pair and the second light source and sensor pair.

7. The method of claim 1, wherein the first sensor is located between the first light source and the probe and the second sensor is located between the second light source and the probe.

8. The method of claim 1, wherein the first sensor and the second sensor are implanted in skin.

9. The method of claim 1, wherein both the first sensor and the second sensor are implanted in muscle.

10. The method of claim 1, wherein the probe is located on the tissue of the patient and each of the first light source and the second light source is located in the tissue of the patient.

11. The method of claim 1, wherein the probe comprises at least one detector that detects the luminescence.

12. The method of claim 1 or 11, wherein the probe comprises an alarm if levels of the analyte reach a threshold value.

13. The method of claim 1 or 11, wherein the probe comprises an alarm prompted by an algorithm operating on current sensor values, past sensor values, or both current and past sensor values of the luminescence.

14. The method of claim 13, wherein the algorithm operates on a summation or area under the sensor signal over time.

15. The method of claim 13, wherein the algorithm operates on a rate of change of sensor values to trigger the alarm.

16. The method of claim 1, wherein each of the first light source and the second light source is selected from the group consisting of light-emitting diode (LED), gas laser, chemical laser, dye laser, metal-vapor laser, solid-state laser, or semiconductor laser.

17. The method of claim 1, wherein each reaction chamber for at least the first sensor and the second sensor is irradiated approximately simultaneously by the first light source attached to the first sensor.

18. The method of claim 1, wherein the first sensor and the second sensor correspond to a plurality of sensors and each sensor of the plurality of sensors is irradiated by a plurality of light sources, wherein each of the plurality of light sources is activated independently.

19. The method of claim 18, wherein each of the plurality of light sources is located adjacent to one reaction chamber such that one light source irradiates one reaction chamber.

20. The method of claim 18 or 19, wherein a wire or a multitude of wires is connected to the plurality of light sources to power the plurality of light sources.

21. The method of claim 20, wherein a portion of the wire or multitude of wires are implanted into the patient, wherein the wire or multitude of wires is utilized as a tether for retrieval of the first light source and sensor pair and the second source and sensor pair.

22. The method of claim 1, wherein the one or more reaction chambers are in communication with a target permeable opening or surface.

23. The method of claim 1, wherein the one or more reaction chambers are in communication with an analyte permeable opening.

24. The method of claim 1, wherein the luminescent dye is a porphyrin dye.

25. The method of claim 1, wherein the analyte is glucose and the molecule is glucose oxidase.

26. The method of claim 1, wherein the analyte is lactate and the molecule is lactate oxidase.

27. The method of claim 1, wherein the analyte is a dissolved gas.

28. The method of claim 1, wherein at least the first sensor and the second sensor further comprise a reference luminescent dye.

29. The method of claim 28, wherein the reference luminescent dye luminesces distinctly from the luminescent dye.

30. The method of claim 28, wherein the reference luminescent dye luminesces similarly to the first luminescent dye.

31. The method of claim 30, wherein the reference luminescent dye associated with the first sensor is irradiated by the first light source such that the reference luminescent dye produces a luminescence.

32. The method of claim 31, wherein the reference luminescent dye is irradiated independently from the first luminescent dye such that the luminescence of the reference luminescent dye is temporally and spatially decoupled from the luminescence from the first luminescent dye.

33. The method of claim 29 or 30, wherein the reference luminescent dye is located in a reference chamber.

34. The method of claim 33, wherein the reference chamber is not fluidly connected to the one or more reaction chambers.

35. The method of claim 1, wherein each of the first sensor and the second sensor comprises at least two different molecules and at least one distinct luminescent dye.

36. The method of claim 1, wherein the molecule is selected from the group consisting of cholesterol oxidase, alcohol oxidase, bilirubin oxidase, ascorbate oxidase, choline oxidase, pyruvate oxidase, sarcosine oxidase, tyramine oxidase, Acyl-CoA oxidase and NADPH oxidase.

37. The method of claim 1, wherein the first light source and sensor pair and the second light source and sensor pair further comprise a reflective element configured to be wirelessly located across tissue.

38. The method of claim 1, wherein the first light source and sensor pair and the second light source and sensor pair further comprise a radio-frequency identification source configured to be wirelessly located across tissue.

39. The method of claim 1, wherein the first light source and sensor pair and the second light source and sensor pair further comprise a magnetic element configured to be wirelessly located across tissue.

40. The method of claim 1, wherein the first light source and sensor pair and the second light source and sensor pair further comprise an electronically conductive element configured to be wirelessly located across tissue.

41. The method of claim 1, wherein the target is oxygen and the breakdown is an oxidative breakdown.

42. The method of claim 1, wherein the inserting of the first light source and sensor pair and the second light source and sensor pair into the patient comprises placing the first light source and sensor pair and the second light source and sensor pair into a lumen of a needle, introducing the first light source and sensor pair and the second light source and sensor pair into the patient using the needle, and removing the needle from the patient, thereby leaving the first light source and sensor pair and the second light source and sensor pair in the patient.

43. The method of claim 1, wherein first light source backlights the first sensor to which it is attached thereto.

* * * * *